(12) United States Patent
Honda et al.

(10) Patent No.: US 11,129,671 B2
(45) Date of Patent: Sep. 28, 2021

(54) ENERGY CONTROL DEVICE, TREATMENT SYSTEM AND ACTUATING METHOD OF ENERGY CONTROL DEVICE

(71) Applicant: OLYMPUS CORPORATION, Tokyo (JP)

(72) Inventors: Yoshitaka Honda, Hachioji (JP); Tsuyoshi Hayashida, Hachioji (JP); Danilo Jr. Baring Legaspi, Hachioji (JP)

(73) Assignee: OLYMPUS CORPORATION, Tokyo (JP)

( * ) Notice: Subject to any disclaimer, the term of this patent is extended or adjusted under 35 U.S.C. 154(b) by 716 days.

(21) Appl. No.: 16/031,166

(22) Filed: Jul. 10, 2018

(65) Prior Publication Data

US 2018/0318000 A1 Nov. 8, 2018

Related U.S. Application Data

(63) Continuation of application No. PCT/JP2016/051120, filed on Jan. 15, 2016.

(51) Int. Cl.
*A61B 18/12* (2006.01)
*A61N 7/02* (2006.01)
(Continued)

(52) U.S. Cl.
CPC .. *A61B 18/1445* (2013.01); *A61B 17/320092* (2013.01); *A61B 18/085* (2013.01);
(Continued)

(58) Field of Classification Search
CPC ... A61B 18/085; A61B 18/10; A61B 18/1206; A61B 18/1445; A61B 2018/0063;
(Continued)

(56) References Cited

U.S. PATENT DOCUMENTS 8,034,049 B2 10/2011 Odom et al.
8,500,735 B2 8/2013 Tanaka et al.
(Continued)

FOREIGN PATENT DOCUMENTS

EP 3000425 A1 3/2016
JP 2007-37568 A 2/2007
(Continued)

OTHER PUBLICATIONS

Sep. 4, 2019 Extended European Search Report issued in European Patent Application No. 16884948.7.
(Continued)

*Primary Examiner* — Daniel W Fowler
(74) *Attorney, Agent, or Firm* — Oliff PLC

(57) ABSTRACT

A controller carries out a single outputting phase in which only first electric energy is supplied to an electrode, and transitions the single outputting phase to a simultaneous outputting phase in which the first electric energy and second electric energy are simultaneously output and treated target is denatured due to both of a high-frequency current and treatment energy generated in a functioning element. The controller sets a control pattern relating to the treatment energy in the simultaneous outputting phase, based on an impedance at a certain time point in the single outputting phase and/or a variation with time of the impedance in the single outputting phase.

20 Claims, 14 Drawing Sheets

(51) Int. Cl.
  *A61B 18/14* (2006.01)
  *A61B 17/32* (2006.01)
  *A61B 18/08* (2006.01)
  *A61B 18/10* (2006.01)
  *A61B 18/00* (2006.01)

(52) U.S. Cl.
  CPC .......... *A61B 18/10* (2013.01); *A61B 18/1206* (2013.01); *A61B 2017/320095* (2017.08); *A61B 2018/0063* (2013.01); *A61B 2018/00642* (2013.01); *A61B 2018/00684* (2013.01); *A61B 2018/00702* (2013.01); *A61B 2018/00875* (2013.01); *A61B 2018/00886* (2013.01); *A61B 2018/00994* (2013.01)

(58) Field of Classification Search
  CPC  A61B 2018/00642; A61B 2018/00684; A61B 2018/00702; A61B 2018/00875; A61B 2018/00886; A61B 2018/00994
  See application file for complete search history.

(56) References Cited

U.S. PATENT DOCUMENTS

| | | | |
|---|---|---|---|
| 8,500,736 | B2 | 8/2013 | Tanaka et al. |
| 2008/0039831 | A1 | 2/2008 | Odom et al. |
| 2008/0058803 | A1 | 3/2008 | Kimura |
| 2009/0076506 | A1* | 3/2009 | Baker ................ A61B 18/1445 606/51 |
| 2009/0248002 | A1* | 10/2009 | Takashino ............ A61B 18/085 606/28 |
| 2011/0077629 | A1 | 3/2011 | Tanaka et al. |
| 2011/0077630 | A1 | 3/2011 | Tanaka et al. |
| 2012/0022521 | A1 | 1/2012 | Odom et al. |
| 2013/0096471 | A1* | 4/2013 | Slayton ............ A61M 37/0092 601/3 |
| 2013/0338740 | A1 | 12/2013 | Honda et al. |
| 2016/0106492 | A1 | 4/2016 | Honda et al. |

FOREIGN PATENT DOCUMENTS

| | | |
|---|---|---|
| JP | 2008-36439 A | 2/2008 |
| JP | 2008-55151 A | 3/2008 |
| JP | 2009-247893 A | 10/2009 |
| WO | 2015/016347 A1 | 2/2015 |

OTHER PUBLICATIONS

May 6, 2020 Office Action issued in Chinese Patent Application No. 201680078869.5.

Mar. 8, 2016 International Search Report issued in International Patent Application No. PCT/JP2016/051120.

* cited by examiner

| Initial impedance Z0 | Arrival time $\Delta$tjudge | Control pattern X |
|---|---|---|
| Z0 > Za | $\Delta$tjudge < $\Delta$ta | X1 |
| Za ≧ Z0 > Zb | $\Delta$ta ≦ $\Delta$tjudge < $\Delta$tb | X2 |
| Zb ≧ Z0 | $\Delta$tb ≦ $\Delta$tjudge | X3 |

FIG. 10A

| Arrival time $\Delta$tjudge \ Initial impedance Z0 | Z0 > Zc | Zc ≧ Z0 |
|---|---|---|
| $\Delta$tjudge < $\Delta$tc | X1 | X2 |
| $\Delta$tc ≦ $\Delta$tjudge | X3 | X3 |

FIG. 10B

| Control pattern X | Temperature T (amplitude U) | Duration $\Delta$tset |
|---|---|---|
| X1 | T1(U1) | $\Delta$t1 |
| X2 | T2(U2) | $\Delta$t2 |
| X3 | T3(U3) | $\Delta$t3 |

(T1 < T2 < T3; U1 < U2 < U3; $\Delta$t1 < $\Delta$t2 < $\Delta$t3)

FIG. 11

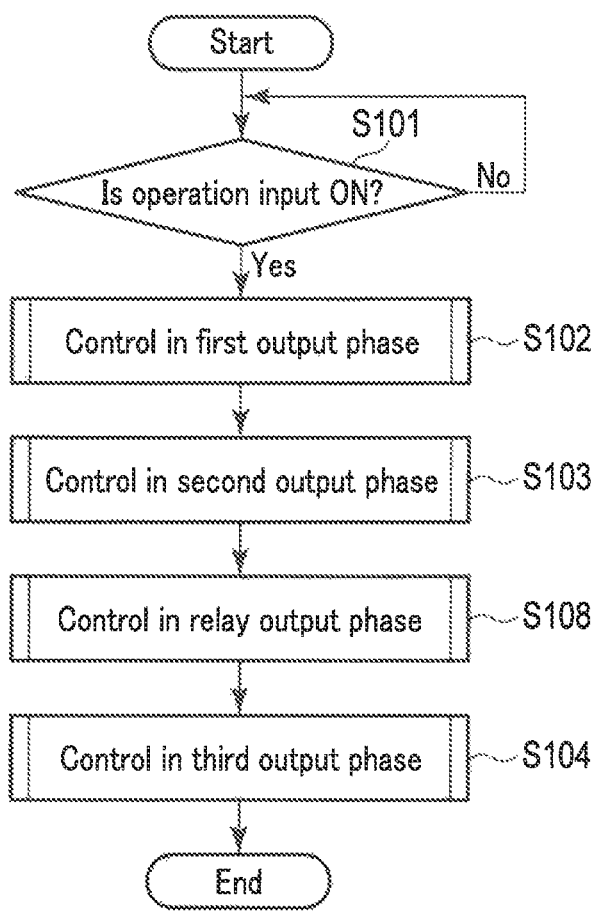
F I G. 16

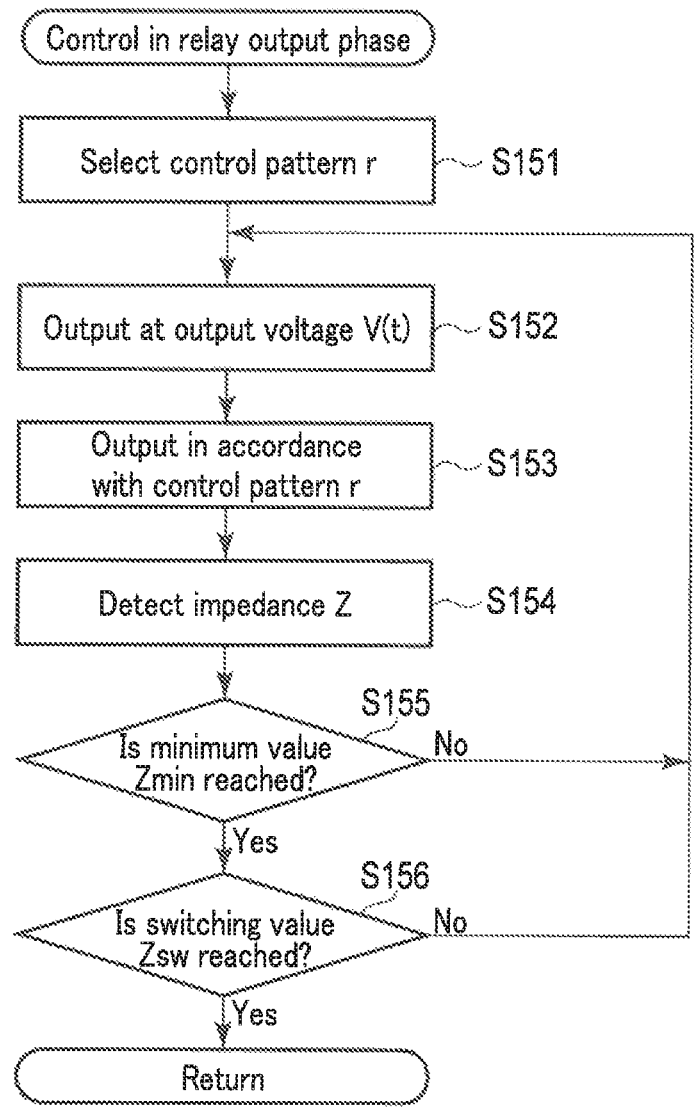
F I G. 19

ENERGY CONTROL DEVICE, TREATMENT SYSTEM AND ACTUATING METHOD OF ENERGY CONTROL DEVICE

CROSS-REFERENCE TO RELATED APPLICATIONS

This is a Continuation Application of PCT Application No. PCT/JP2016/051120, filed Jan. 15, 2016, the entire contents of which are incorporated herein by reference.

BACKGROUND OF THE INVENTION

1. Field of the Invention

The present invention relates to an energy control device controlling the supply of energy to an energy treatment instrument which treats a treated target by using energy, and a treatment system including the energy control device. Further, the invention relates to an actuating method of this energy control device.

2. Description of the Related Art

U.S. Patent Application Publication No. 2013/338740 discloses an energy treatment instrument in which electrodes and a heat generating body are provided in an end effector, and an energy control device which controls the supply of energy to the energy treatment instrument. In this energy treatment instrument, first electric energy is supplied from the energy control device to the electrodes. Thereby, a high-frequency current flows through a treated target which is grasped by the end effector. In addition, second electric energy is supplied from the energy control device to the heat generating body. Thereby, heat is generated by the heat generating body, and the generated heat is applied to the treated target grasped by the end effector. In a treatment, a first output phase, in which only the first electric energy supplied to the electrodes is output from the energy control device, is continued from an output start. Then, when an impedance of the grasped treated target reaches a switching value, the first output phase is switched to a second output phase in which only the second electric energy supplied to the heat generating body is output from the energy control device. Until a certain length of time passes from the start of the second output phase, a constant temperature control, which keeps with time the heat generating body at a predetermined temperature, is executed according to the output of the second electric energy.

BRIEF SUMMARY OF THE INVENTION

According to one aspect of the invention, an energy control device configured to control supply of energy to an energy treatment instrument, the energy treatment instrument including an electrode and a functioning element, the energy control device including: a first energy output source configured to output first electric energy, and configured to pass a high-frequency current through a treated target by supplying the output first electric energy to the electrode; a second energy output source configured to output second electric energy different from the first electric energy, and configured to generate treatment energy different from the high-frequency current in the functioning element by supplying the output second electric energy to the functioning element; and a controller configured to control an output of the first electric energy from the first energy output source and an output of the second electric energy from the second energy output source, the controller being configured to execute: carrying out a single outputting phase in which only the first electric energy is output; detecting an impedance of the treated target with time in the single outputting phase; transitioning the single outputting phase to a simultaneous outputting phase in which the first electric energy and the second electric energy are simultaneously output and the treated target is denatured due to both of the high-frequency current and the treatment energy; and setting a control pattern relating to the treatment energy in the simultaneous outputting phase, based on at least one of the impedance at a certain time point in the single outputting phase and a variation with time of the impedance in the single outputting phase, and controlling the output of the second electric energy in the simultaneous outputting phase, based on the set control pattern.

According to one another aspect of the invention, an actuating method of an energy control device, the energy control device being configured to control supply of energy to an energy treatment instrument, the energy treatment instrument including an electrode and a functioning element, the actuating method including: outputting first electric energy, and then passing a high-frequency current through a treated target by supplying the output first electric energy to the electrode; outputting second electric energy different from the first electric energy, and then generating treatment energy different from the high-frequency current in the functioning element by supplying the output second electric energy to the functioning element; and controlling an output of the first electric energy and an output of the second electric energy, the controlling the output of the first electric energy and the output of the second electric energy including: carrying out a single outputting phase in which only the first electric energy is output; detecting an impedance of the treated target with time in the single outputting phase; transitioning the single outputting phase to a simultaneous outputting phase in which the first electric energy and the second electric energy are simultaneously output and the treated target is denatured due to both of the high-frequency current and the treatment energy; and setting a control pattern relating to the treatment energy in the simultaneous outputting phase, based on at least one of the impedance at a certain time point in the single outputting phase and a variation with time of the impedance in the single outputting phase, and controlling the output of the second electric energy in the simultaneous outputting phase, based on the set control pattern.

Advantages of the invention will be set forth in the description which follows, and in part will be obvious from the description, or may be learned by practice of the invention. The advantages of the invention may be realized and obtained by means of the instrumentalities and combinations particularly pointed out hereinafter.

BRIEF DESCRIPTION OF THE SEVERAL VIEWS OF THE DRAWING

The accompanying drawings, which are incorporated in and constitute a part of the specification, illustrate embodiments of the invention, and together with the general description given above and the detailed description of the embodiments given below, serve to explain the principles of the invention.

FIG. 10A is a schematic view for describing a process of determining a control pattern of the output control of second electric energy in a third output phase in each of one example and another example of the first embodiment;

FIG. 10B is a schematic view for describing a process of determining a control pattern of the output control of the second electric energy in the third output phase in still another example of the first embodiment;

FIG. 11 is a schematic view illustrating a relationship of a parameter relating to treatment energy and a duration of the third output phase relative to a control pattern of the output control of the second electric energy in the third output phase, in each of one example and another example of the first embodiment;

FIG. 16 is a flowchart illustrating a process in a treatment, which is executed by the controller of an energy control device according to a fourth modification;

FIG. 19 is a flowchart illustrating a process which the controller according to the fourth modification executes in the control in the relay output phase.

DETAILED DESCRIPTION OF THE INVENTION

First Embodiment

A first embodiment of the present invention will be described with reference to FIG. 1 to FIG. 12.

Figure 1:
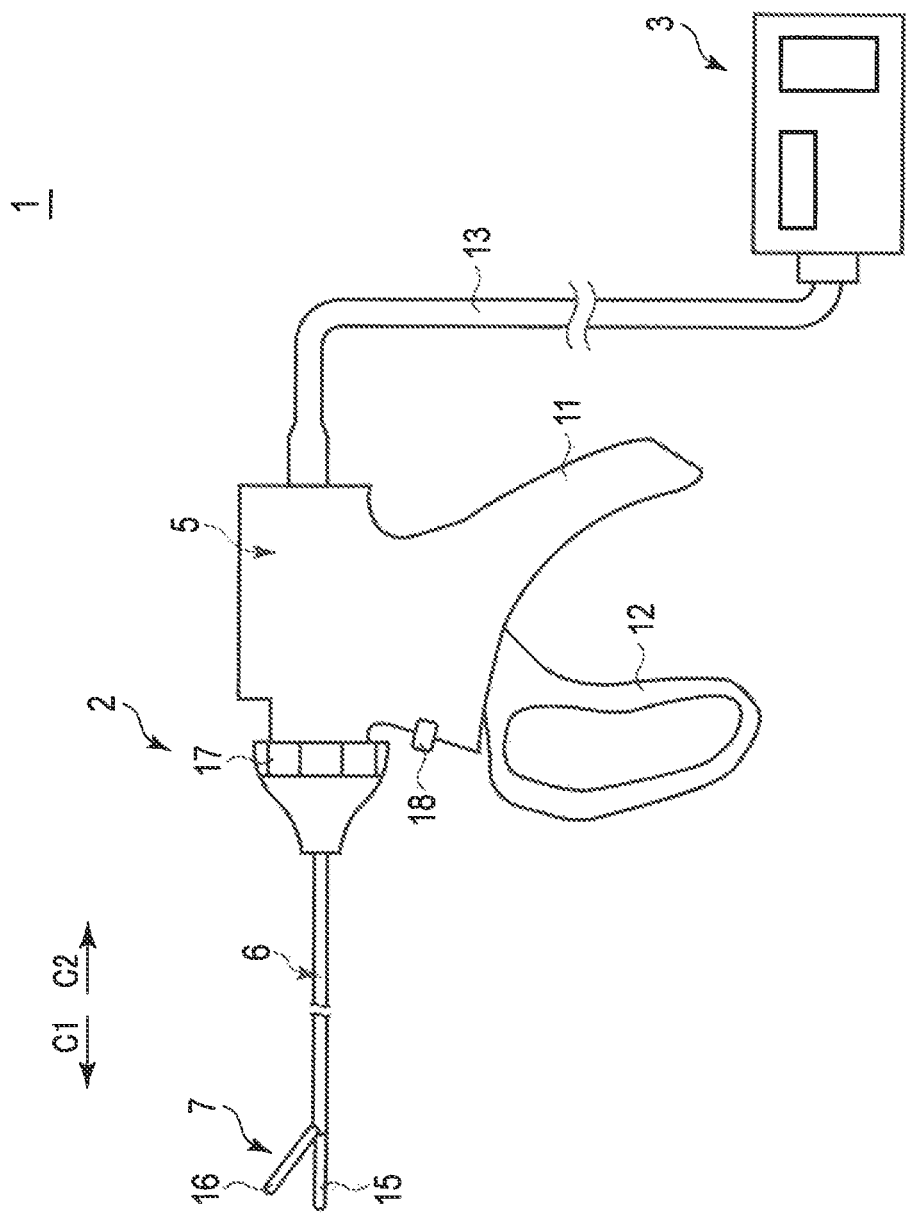
FIG. 1 is a schematic view illustrating a treatment system according to a first embodiment.

FIG. 1 is a view illustrating a treatment system 1 of the present embodiment. As illustrated in FIG. 1, the treatment system 1 includes an energy treatment instrument 2 and an energy control device 3 which controls the supply of energy to the energy treatment instrument 2. Here, in FIG. 1, an arrow C1 side is defined as a distal side, and an arrow C2 side (a side opposite to the distal side) is defined as a proximal side.

The energy treatment instrument 2 includes a housing 5 which can be held, a shaft 6 which is coupled to the distal side of the housing 5, and an end effector 7 provided in a distal portion of the shaft 6. A grip 11 is provided in the housing 5, and a handle 12 is rotatably attached to the housing 5. By the handle 12 rotating relative to the housing 5, the handle 12 opens or closes relative to the grip 11.

The end effector 7 comes in contact with a treated target in a treatment, and includes a first grasping piece 15 and a second grasping piece 16. By opening or closing the handle 12 relative to the grip 11, the paired grasping pieces 15 and 16 open or close relative to each other. Thereby, a treated target such as a blood vessel (biological tissue) can be grasped between the paired grasping pieces 15 and 16. Note that one of the grasping pieces 15 and 16 may be rotatably attached to a distal portion of the shaft 6, or both of the grasping pieces 15 and 16 may be rotatably attached to the distal portion of the shaft 6. Besides, a rod member (not shown), which is inserted through the sheath 6, may be provided, and one of the grasping pieces 15 and 16 (e.g. first grasping piece 15) may be formed by a projecting portion of the rod member, which projects from the sheath 6 toward the distal side. In addition, in this embodiment, a rotation knob 17 is rotatably attached to the housing 5. By the rotation knob 17 rotating relative to the housing 5, the shaft 6 and end effector 7 rotate together with the rotation knob 17 around the center axis of the shaft 6 relative to the housing 5.

One end of a cable 13 is connected to the housing 5. The other end of the cable 13 is detachably attached to the energy control device 3. In addition, an operation button functioning as an energy operation input portion is attached to the housing 5. By pushing the operation button 18, an operation (signal), which causes the energy control device 3 to output energy to the energy treatment instrument 2, is input to the energy control device 3. In place of the operation button 18 or in addition to the operation button 18, a footswitch or the like, which is separate from the energy treatment instrument 2, may be provided as the energy operation input portion.

Figure 2:
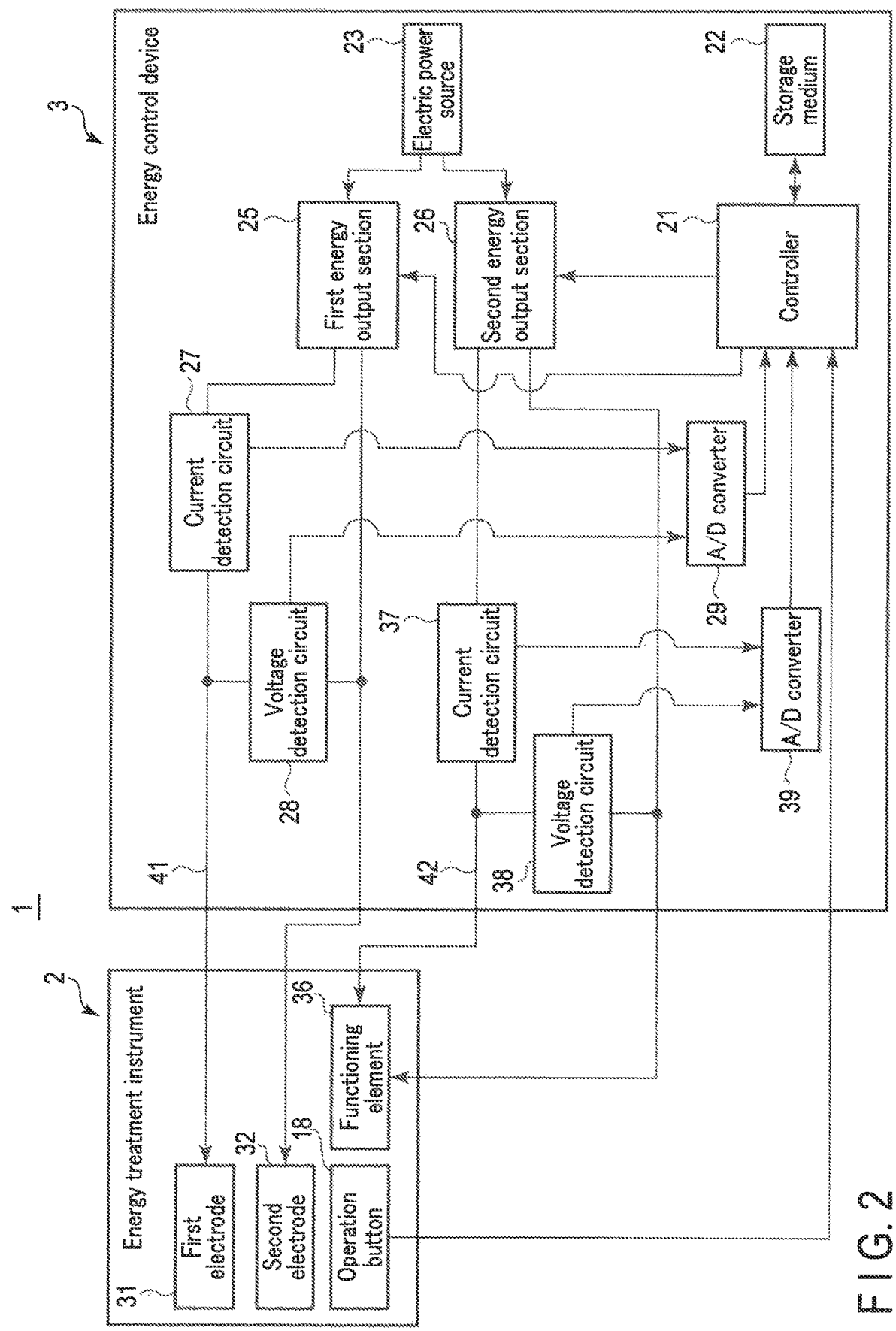
FIG. 2 is a block diagram which schematically illustrates a configuration which supplies energy to an energy treatment instrument from an energy control device according to the first embodiment.

FIG. 2 is a view illustrating a configuration which supplies energy (first electric energy and second electric energy) to the energy treatment instrument 2 from the energy control device 3. As illustrated in FIG. 2, the energy control device 3 includes a controller 21 which controls the entirety of the treatment system, and a storage medium 22. The controller (control circuit) 21 is formed of an integrated circuit or a processor including a CPU (Central Processing Unit), an ASIC (Application Specific Integrated Circuit) or an FPGA (Field Programmable Gate Array). The controller 21 may be formed of a single integrated circuit or the like, or may be formed of a plurality of integrated circuits or the like. The process in the controller 21 is executed according to a program stored in the controller 21 or storage medium 22. In addition, the storage medium 22 stores a processing program which is used in the controller 21, and parameters, tables, etc. which are used in calculations in the controller 21. The controller 21 detects the presence or absence of an operation input by the energy operation input portion such as the operation button 18.

In addition, the energy control device 3 includes an electric power source 23 such as a battery or a plug socket, a first energy output section (first energy output source) 25 and a second energy output section (second energy output source) 26. The first energy output section is a driving circuit or the like, which includes a conversion circuit, an amplifier, etc., and converts electric power from the electric power source 23 to first electric energy. In addition, the converted first electric energy is output from the first energy output section 25. Besides, the second energy output section 26 is a driving circuit or the like, which includes a conversion circuit, an amplifier, etc., and converts electric power from the electric power source 23 to second electric energy which is different from the first electric energy. In addition, the converted second electric energy is output from the second energy output section 26. The controller 21 controls the driving of each of the energy output sections 25 and 26, and controls the output of the first electric energy from the first energy output section 25 and the output of the second electric energy from the second energy output section 26. By the control in the controller 21, output electric power P, output current I and output voltage V of the first electric energy are adjusted, and output electric power P', output current I' and output voltage V' of the second electric energy are adjusted.

The end effector 7 of the energy treatment instrument is provided with a first electrode 31 and a second electrode 32. For example, the first electrode 31 is provided in the first grasping piece 15, and the second electrode 32 is provided in the second grasping piece 16. The first electric energy, which is output from the first energy output section (first driving circuit) 25, is supplied to the electrodes 31 and 32. Accordingly, a first supply circuit 41, which supplies the first electric energy, is formed between the first energy output section 25 and the electrodes 31 and 32 through the inside of the energy control device 3, the inside of the cable 13 and the energy treatment instrument 2. Here, the first electric energy is high-frequency electric energy (high-frequency electric power). Thus, by the first electric energy being supplied to the electrodes 31 and 32 in the state in which the treated target is grasped between the grasping pieces 15 and 16, a high-frequency current flows between the electrodes 31 and 32 through the grasped treated target. By the high-frequency current flowing through the treated target, heat is generated in the treated target, and the treated target is denatured by the heat.

The first supply circuit 41 is provided with a current detection circuit 27 and a voltage detection circuit 28. In the state in which the first electric energy is being output from the first energy output section 25, the current detection circuit 27 detects a current value of the output current I, and the voltage detection circuit 28 detects a voltage value of the output voltage V. The energy control device 3 is provided with an A/D converter 29. An analog signal indicative of the current value detected by the current detection circuit 27 and an analog signal indicative of the voltage value detected by the voltage detection circuit 28 are transmitted to the A/D converter 29. The A/D converter 29 converts the analog signal indicative of the current value and the analog signal indicative of the voltage value to digital signals, and transmits the converted digital signals to the controller 21.

In the state in which the first electric energy is being output from the first energy output section 25, the controller 21 acquires information relating to the output current I and output voltage V of the first electric energy. Then, based on the output current I and output voltage V, the controller 21 detects the impedance of the first supply circuit 41 including the grasped treated target and the electrodes 31 and 32. Thereby, an impedance of the grasped treated target is detected. Specifically, in the state in which the first electric energy is being output from the first energy output section 25, the impedance (tissue impedance) of the treated target is detected with time, based on the output current I and output voltage V of the first electric energy.

A functioning element 36 is provided in the end effector 7 of the energy treatment instrument 2. The second electric energy, which is output from the second energy output section (second driving circuit) 26, is supplied to the functioning element 36. Accordingly, a second supply circuit 42, which supplies the second electric energy, is formed between the second energy output section 26 and the functioning element 36 through the inside of the energy control device 3, the inside of the cable 13 and the energy treatment instrument 2. By the second electric energy being supplied to the functioning element 36, treatment energy that is different from the high-frequency current is generated by the functioning element 36.

The second supply circuit 42 is provided with a current detection circuit 37 and a voltage detection circuit 38. In the state in which the second electric energy is being output from the second energy output section 26, the current detection circuit 37 detects a current value of the output current I', and the voltage detection circuit 38 detects a voltage value of the output voltage V'. The energy control device 3 is provided with an A/D converter 39. An analog signal indicative of the current value detected by the current detection circuit 37 and an analog signal indicative of the voltage value detected by the voltage detection circuit 38 are transmitted to the A/D converter 39. The A/D converter 39 converts the analog signal indicative of the current value and the analog signal indicative of the voltage value to digital signals, and transmits the converted digital signals to the controller 21.

In the state in which the second electric energy is being output from the second energy output section 26, the controller 21 acquires information relating to the output current I' and output voltage V' of the second electric energy. Then, based on the output current I' and output voltage V', the controller 21 detects the impedance of the second supply circuit 42 including the functioning element 36.

Figure 3:
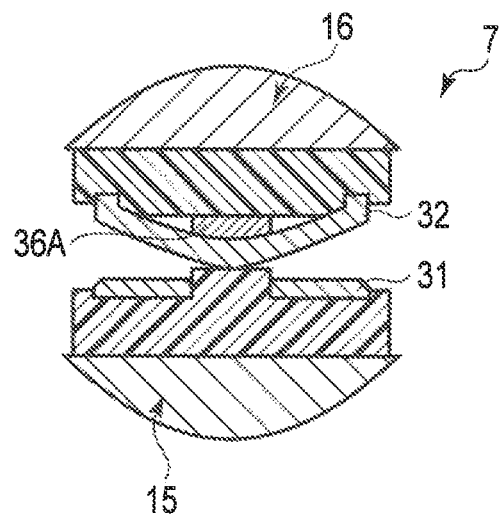
FIG. 3 is a schematic view for describing a functioning element according to one example of the first embodiment.

FIG. 3 illustrates the functioning element 36 of one example. In the example of FIG. 3, a heat generating body 36A is provided in the end effector 7 as the functioning element 36. Note that in this example, the heat generating body 36A is provided in the second grasping piece 16, but the heat generating body 36A may be provided in at least one of the grasping pieces 15 and 16. By the second electric energy being supplied to the heat generating body 36A, heat is generated by the heat generating body 36A as the treatment energy. The heat generated by the heat generating body 36A is transmitted to the end effector 7, and is applied to the treated target. Thereby, the treated target is denatured by the heat generated by the heat generating body 36A.

In this example, DC electric power or AC electric power is supplied as the second electric energy. An amount of the generating heat (Joule heat) Q generated by the heat generating body 36A increases if the output electric power P' of the second electric energy is increased. In addition, the amount of the generating heat Q in the heat generating body 36A (i.e. heat energy generated as treatment energy) increases in each of the case in which the output current I' is increased and the case in which the output voltage V' is increased.

In this example, based on the output current I' and output voltage V' of the second electric energy, the controller 21 detects the resistance (variable resistance) R of the heat generating body 36A with time. The amount of the generating heat Q in the heat generating body 36A varies in accordance with the resistance R of the heat generating body 36A. Thus, by the variation of the resistance R of the heat generating body 36A, the amount of the generating heat Q in the heat generating body 36A varies, and a temperature T of the end effector 7 (treated target) varies. In this example, the controller 21 detects with time the temperature T of the end effector 7, based on the resistance R of the heat generating body 36A. In this case, a table or the like, which shows the relationship between the resistance R of the heat generating body 36A and the temperature T of the end effector 7, is stored in the storage medium 22.

Figure 4:
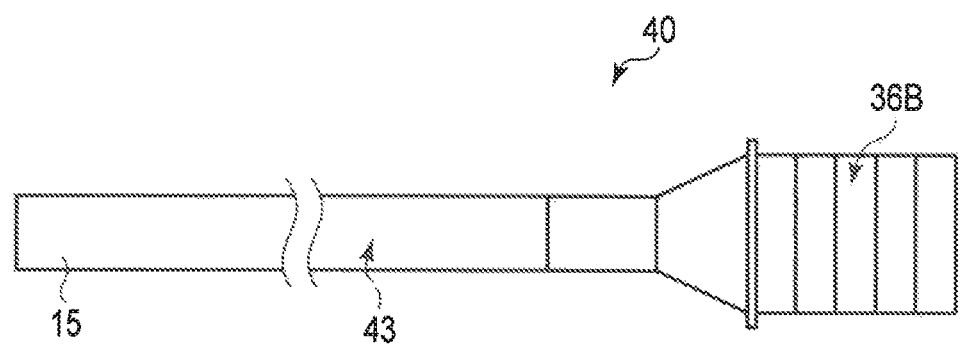
FIG. 4 is a schematic view for describing a functioning element according to another example of the first embodiment.

FIG. 4 illustrates the functional element 36 of another example. In the example of FIG. 4, an ultrasonic transducer 36B is provided in the inside of the housing 5 as the functioning element 36. By the second electric energy being supplied to the ultrasonic transducer 36B, ultrasonic vibration is generated by the ultrasonic transducer 36B as treatment energy. In this example, a vibration transmitting member (rod member) 43 is inserted through the shaft 6, and the first grasping piece 15 is formed by a projecting portion of the vibration transmitting member 43, which projects from the sheath 6 toward the distal side. In addition, a vibrating body 40 is formed by the ultrasonic transducer 36B and vibration transmitting member 43. Ultrasonic vibration generated by the ultrasonic transducer 36B is transmitted to the first grasping piece 15 of the end effector 7. In the state in which the treated target is grasped between the grasping pieces 15 and 16, the vibration transmitting member 43 vibrates by the ultrasonic vibration, and thereby frictional heat is generated between the treated target and the first grasping piece 15. The treated target is denatured by the generated frictional heat.

In this example, AC electric power of a predetermined frequency is supplied as the second electric energy. Thereby, the vibrating body 40 including the ultrasonic transducer 36B and vibration transmitting member 43 vibrates at a predetermined resonance frequency. An amplitude U and vibration velocity v (i.e. vibration energy generated as treatment energy) in the vibrating body 40 increase if the output current I' of the second electric energy is increased. In this example, based on the output current I' of the second electric energy, the controller 21 detects with time the amplitude U and vibration velocity v in the vibrating body 40. In this case, a table or the like, which shows the relationship of the amplitude U and vibration velocity v in the vibrating body 40 to the output current I' of the second electric energy, is stored in the storage medium 22. In addition, in this example, based on the output current I' and output voltage V' of the second electric energy, the controller 21 detects with time an acoustic impedance Z' of the vibrating body 40. The acoustic impedance Z' is indicative of a load on the vibration of the vibrating body 40.

Note that the energy control device 3 may be provided with a dial, a touch panel or the like as a level setter (not shown) which sets energy levels of the first electric energy and second electric energy. In this case, based on the set energy level, the controller 21 controls the output from each of the energy output section 25, 26. In addition, the energy control device 3 may be provided with a monitor or the like as a display (not shown) on which the set energy levels of the first electric energy and second electric energy are displayed, and may be provided with a buzzer or the like as an alert section (not shown) which produces alert sound, etc. In this case, the actuations of the display and alert section are controlled by the controller 21.

Next, the function and advantageous effects of the energy control device 3 and treatment system 1 will be described. When a treatment is performed by the treatment system 1, the energy treatment instrument 2 is connected to the energy control device 3 via the cable 13. Then, each of the energy levels of the first electric energy and second electric energy, which are output, is set in a desired energy range. Further, the end effector 7 of the energy treatment instrument 2 is inserted in the inside of a body cavity such as an abdominal cavity. Then, in the state in which a treated target such as a biological tissue is located between the grasping pieces 15 and 16, the handle 12 is closed relative to the grip 11. Thereby, the grasping pieces 15 and 16 close relative to each other, and the treated target is grasped between the grasping pieces 15 and 16. By an operation input being performed by the operation button 18 in the state in which the treated target is grasped, the outputs of the first electric energy and second electric energy are controlled as will be described later, and the treated target is treated.

Figure 5:
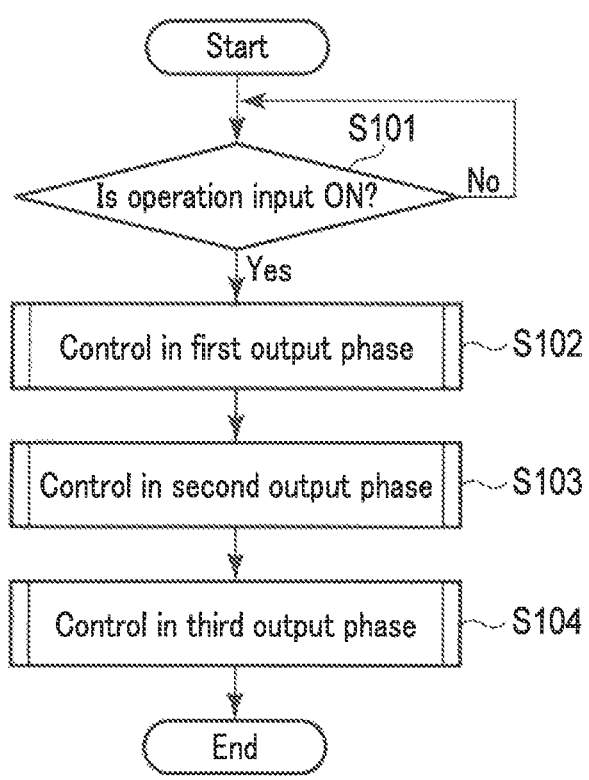
FIG. 5 is a flowchart illustrating a process in a treatment, which is executed by a controller of the energy control device according to the first embodiment.

FIG. 5 is a flowchart illustrating a process which is executed by the controller 21 of the energy control device 3 in a treatment. As illustrated in FIG. 5, the controller 21 judges whether an operation input was performed by the operation button (energy operation input portion) 18 (i.e. whether an operation input is ON or OFF) (step S101). If the operation input is not performed (step S101—No), the process returns to step S101. In other words, the controller 21 stands by until the operation input is performed by the operation button 18. If the operation input is performed (step S101—Yes), the controller 21 executes control in a first output phase (step S102). If the control in the first output phase ends, the controller 21 executes control in a second output phase (step S103). If the control in the second output phase ends, the controller 21 executes control in a third output phase (step S104). In this embodiment, if the third output phase ends, the output control of the first electric energy and second electric energy by the controller 21 terminates. The transition from the control in the first output phase to the control in the second output phase is successively executed without a time lag. The transition from the control in the second output phase to the control in the third output phase is successively executed without a time lag.

Figure 6:
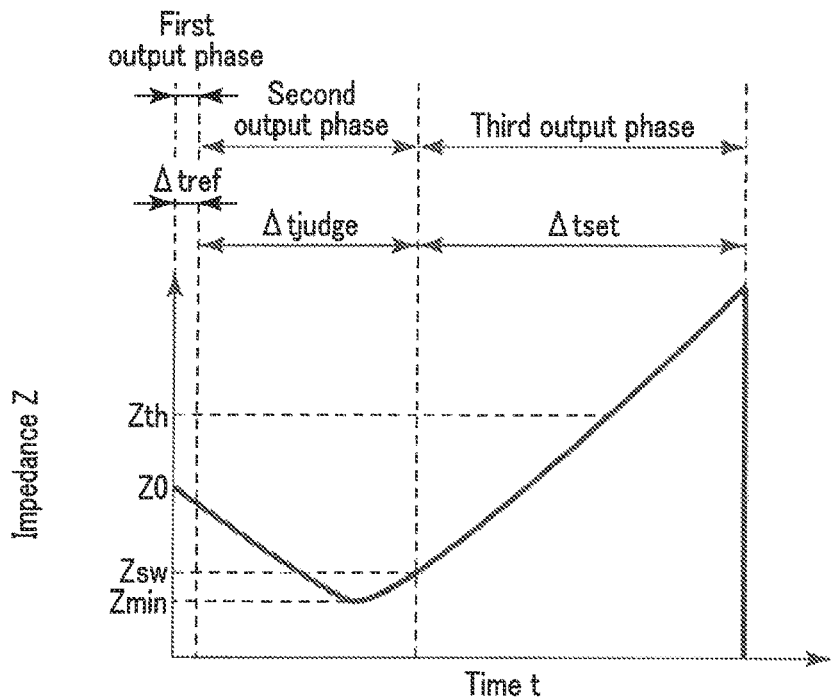
FIG. 6 is a schematic view illustrating an example of a variation with time of an impedance of a treated target in a treatment using the energy control device according to the first embodiment.
Figure 7:
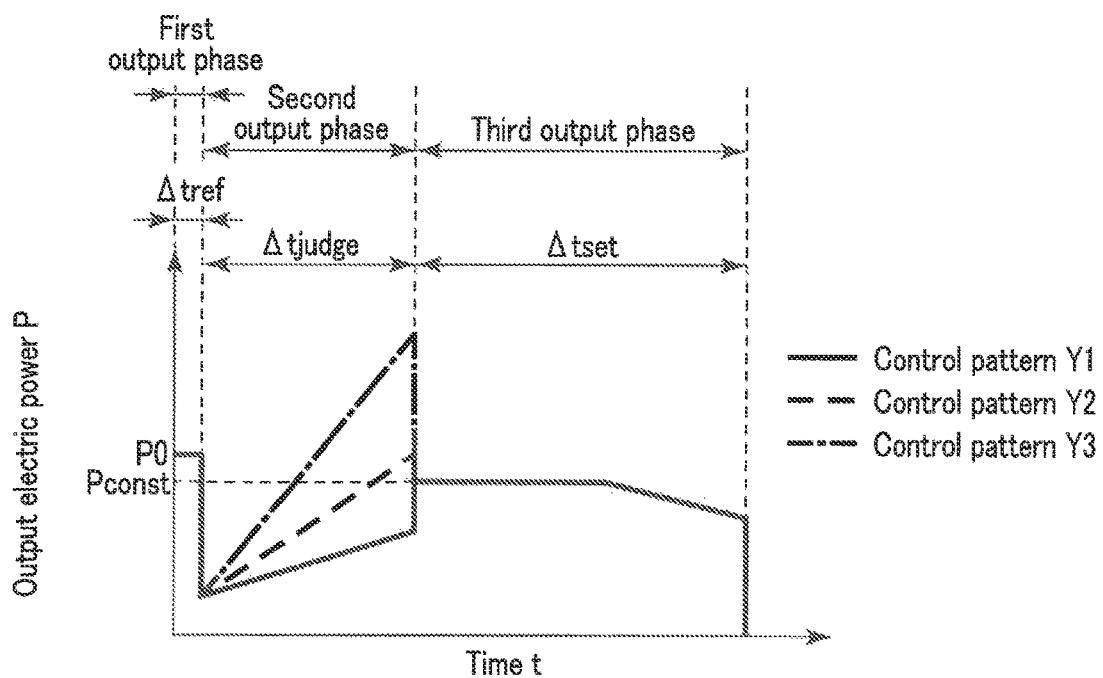
FIG. 7 is a schematic view illustrating an example of a variation with time of output electric power of first electric energy in the treatment using the energy control device according to the first embodiment.

FIG. 6 is a view illustrating an example of a variation with time of an impedance (tissue impedance) Z of a treated target in a treatment, and FIG. 7 is a view illustrating an example of a variation with time of output electric power P of the first electric energy in the treatment. In FIG. 6 and FIG. 7, the abscissa axis indicates time t with reference to a control start (an output start of the first electric energy) in the first output phase. In addition, the ordinate axis in FIG. 6 indicates an impedance Z of a treated target, and the ordinate axis in FIG. 7 indicates output electric power P.

As illustrated in FIG. 6 and FIG. 7, in the present embodiment, in each of the first output phase to the third output phase, the first electric energy is output from the first energy output section 25. Thus, in each of the first output phase to the third output phase, high-frequency current flows through the grasped treated target. In addition, the treated target is denatured by the heat occurring due to the high-frequency current, and the treated target is sealed.

Besides, in this embodiment, in each of the first output phase to the third output phase, the impedance Z of the treated target is detected with time, based on the output current I and output voltage V of the first electric energy. Here, if the output of the first electric energy is started and the high-frequency current begins to flow through the treated target, the impedance Z decreases with time until the moisture in the treated target (in the biological tissue) is evaporated by the heat due to the high-frequency current. Then, after the moisture in the treated target is evaporated, the temperature of the treated target rises by the heat due to the high-frequency current and, accordingly, the impedance Z increases with time. Thus, the impedance Z decreases with time to a minimum value Zmin from the output start of the first electric energy (the output start in the first output phase), and the impedance Z increases with time after the impedance Z takes the minimum value Zmin.

Moreover, in this embodiment, the first output phase and second output phase become a single outputting phase in which only the first electric energy is output and the second electric energy is not output from the second energy output section 26. Thus, in the first output phase and second output phase, the second electric energy is not supplied to the functioning element 36, and the treatment energy (heat or ultrasonic vibration, etc.) is not generated by the functioning element 36 (heat generating body 36A or ultrasonic transducer 36B, etc.). Accordingly, in the single outputting phase, the treated target is denatured due to only the high-frequency current flowing through the treated target. In this embodiment, the single outputting phase is continued from the output start of the first electric energy.

Besides, the third output phase becomes a simultaneous outputting phase in which both the first electric energy and the second electric energy are simultaneously output. Thus, in the third output phase, the second electric energy is supplied to the functioning element 36, and the treatment energy is generated by the functioning element 36. Accordingly, in the simultaneous outputting phase, the treated target is denatured due to both the high-frequency current flowing through the treated target and the treatment energy (heat or ultrasonic vibration, etc.) generated by the functioning element 36. At this time, the treated target is sealed due to the high-frequency current, and the treated target is cut and opened and, at the same time, sealed due to the treatment energy. By the switching from the second output phase to the third output phase, the single outputting phase transitions to the simultaneous outputting phase.

Figure 8:
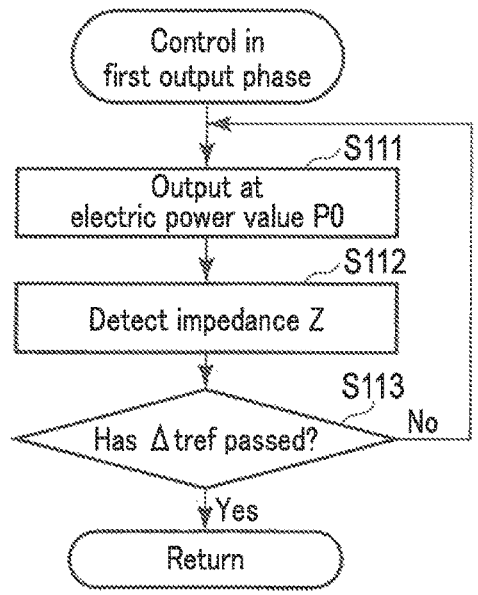
FIG. 8 is a flowchart illustrating a process which the controller according to the first embodiment executes in the control in a first output phase.

FIG. 8 is a flowchart illustrating a process which is executed by the controller 21 in the control in the first output phase. As illustrated in FIG. 8, in the control in the first output phase, the controller 21 outputs the first electric energy (high-frequency electric power) at an electric power value P0, and supplies the first electric energy of the electric power value P0 to the electrodes 31 and 32 (step S111). Then, the controller 21 acquires the output current I and output voltage V of the first electric energy from the current detection circuit 27 and voltage detection circuit 28, and detects the impedance Z of the treated target, based on the output current I and output voltage V (step S112).

Then, the controller 21 judges whether a reference time Δtref has passed since the start of the first output phase (the output start of the first electric energy) (step S113). The reference time Δtref may be set by a surgeon, or may be stored in the storage medium 22. In addition, it is preferable that the reference time Δtref is shorter than a time from the start of the first output phase until the impedance Z reaches the minimum value Zmin, and is about 100 ms. If the reference time Δtref has not passed (step S113—No), the process returns to step S111, and the output of the first electric energy at the electric power value P0 (step S111) and the detection of the impedance Z (step S112) are repeated. If the reference time Δtref has passed (step S113—Yes), the control in the first output phase ends, and the first output phase transitions to the second output phase.

By the execution of the above-described process, in the first output phase, constant electric power control, which keeps the output electric power P of the first electric energy constant with time at the electric power value P0, is executed during the reference time Δtref. In addition, since the reference time Δtref is shorter than the time from the start of the first output phase until the impedance Z reaches the minimum value Zmin, the first output phase ends before the impedance Z reaches the minimum value Zmin.

Besides, the impedance Z of the treated target, which is detected in the first output phase, is set as an initial impedance Z0. The initial impedance Z0 may be an impedance Z at the time of the output start of the first electric energy, or may be an intermediate value or a mean value of the impedance Z during the first output phase (reference time Δtref). Specifically, in the single outputting phase, the impedance Z at the time of the output start of the first electric energy or immediately thereafter is detected as the initial impedance Z0.

In the second output phase, the output of the first electric energy is controlled based on the initial impedance Z0 detected in the first output phase. In one example, in the second output phase, the controller 21 adjusts, based on the initial impedance Z0, an output voltage V(t) of the first electric energy at time t, and controls the output of the first electric energy. In addition, for example, the output of the first electric energy is controlled in such a state that the following equation (1) is established with respect to the output voltage (the voltage between the electrodes 31 and 32) V(t) at time t.

$$V(t) = \alpha t + \beta \quad (1)$$

In this case, in the second output phase, the output voltage V(t) increases with time in a manner of a linear function (linearly). Here, α in equation (1) indicates an increase rate with time of the output voltage V(t) in the second output phase, and is determined based on the initial impedance Z0. In addition, β in equation (1) is a constant. In this example, by the determination of the increase rate α with time of the output voltage V(t), control patterns Y (Y1, Y2, Y3) relating to the output control of the first electric energy in the second output phase are determined. Note that, in this example, although the output control of the first electric energy in the second output phase is executed based on any one of three control patterns Y1, Y2 and Y3, the output control is not limited to this example. Specifically, the number of control patterns Y of the output control of the first electric energy in the second output phase may be two or four, if the control patterns Y are classified into plural control patterns Y. Besides, the output control of the first electric energy in the second output phase may be executed by only one control pattern Y, regardless of the initial impedance Z0.

For example, when the output control of the first electric energy is executed by the control pattern Y2, the increase rate α is set to be greater than when the output control of the first electric energy is executed by the control pattern Y1. In addition, when the output control is executed by the control pattern Y3, the increase rate α is set to be greater than when the output control is executed by the control pattern Y2. Thereby, when the output control is executed by the control pattern Y2, an increase rate α' with time of the output electric power P is greater than when the output control is executed by the control pattern Y1, and when the output control is executed by the control pattern Y3, the increase rate α' with time of the output electric power P is greater than when the output control is executed by the control pattern Y2 (see FIG. 7). In FIG. 7, in the second output phase, the variation with time of the output electric power P of the first electric energy is indicated by a solid line when the output control is executed by the control pattern Y1, is indicated by a broken line when the output control is executed by the control pattern Y2, and is indicated by a dot-and-dash line when the output control is executed by the control pattern Y3.

Here, for example, when the treated target is a blood vessel which is thin (small in volume v), there are a less number of paths of flow of electric current than in the case of a thick blood vessel, and the amount of moisture included in the treated target becomes smaller, and it is thus relatively difficult for a high-frequency current to flow through the treated target. Hence, the initial impedance Z0 detected in the first output phase becomes higher than in the case of the thick blood vessel. In this case, the output control of the first electric energy is executed by the control pattern Y (e.g. control pattern Y1) with a small increase rate α with time of the output voltage V(t). On the other hand, when the treated target is a blood vessel which is thick (large in volume v), there are a greater number of paths of flow of electric current than in the case of a thin blood vessel, and the amount of moisture included in the treated target becomes larger, and it is thus relatively easy for a high-frequency current to flow through the treated target. Hence, the detected initial impedance Z0 becomes lower than in the case of the thin blood vessel. In this case, the output control of the first electric energy is executed by the control pattern Y (e.g. control pattern Y3) with a large increase rate α with time of the output voltage V(t).

In another example, in the second output phase, the output control of the first electric energy may be executed in such a state that the output voltage V(t) increases with time in a nonlinear manner such as a quadratic function manner or an exponential function manner. In this case, too, the increase rate α with time of the output voltage V(t) is adjusted based on the initial impedance Z0. In still another example, in the second output phase, the output control of the first electric energy may be executed in such a state that the output electric power P(t) or output current I(t) increases with time in a linear manner or in a nonlinear manner. In this case, the increase rate α' with time of the output electric power P(t) or an increase rate α" with time of the output current I(t) may be adjusted based on the initial impedance Z0.

Figure 9:
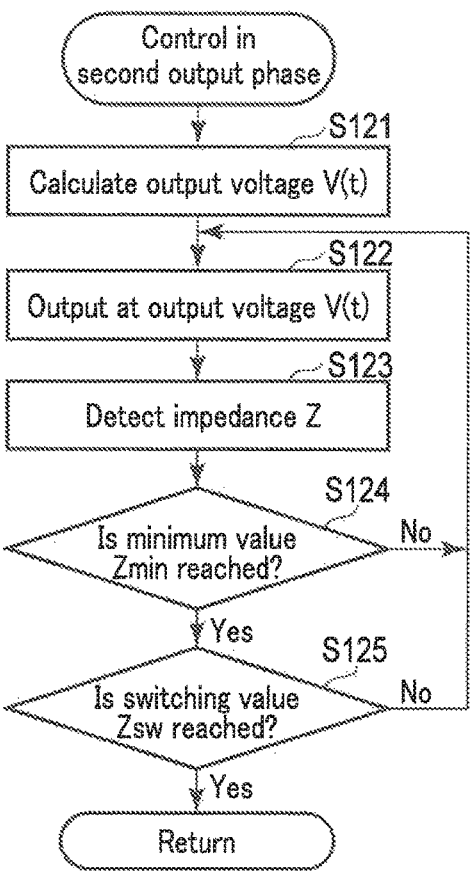
FIG. 9 is a flowchart illustrating a process which the controller according to the first embodiment executes in the control in a second output phase.

FIG. 9 is a flowchart illustrating a process which is executed by the controller 21 in the control in the second output phase. Here, a description is given of an example in which output control to linearly increase with time the output voltage V(t) in the second output phase is executed. As illustrated in FIG. 9, in the control in the second output phase, the controller 21 calculates the output voltage V(t) at each time t, based on the initial impedance Z0 detected in the first output phase (step S121). At this time, based on the initial impedance Z0, the controller 21 determines the above-described control pattern Y and the increase rate α with time of the output voltage V(t), and calculates the output voltage V(t). Then, the controller 21 causes the first energy output section 25 to output the first electric energy at the output voltage V(t) corresponding to the time t (step S122). In addition, the controller 21 detects the impedance Z of the treated target, based on the output current I and output voltage V (step S123).

Then, the controller 21 judges whether the impedance Z of the treated target reached the minimum value Zmin (step S124). After the impedance Z reached the minimum value Zmin (step S124—Yes), the controller 21 judges whether the impedance Z reached a switching value Zsw (step S125). In each of the case in which the impedance Z does not reach the minimum value Zmin (step S124—No) and the case in which the impedance Z does not reach the switching value Zsw (step S125—No), the process returns to step S122, and the output of the first electric energy at the output voltage V(t) (step S122) and the detection of the impedance Z (step S123) are repeated. If the impedance Z reached the switching value Zsw (step S125—Yes), the control in the second output phase is finished, and the second output phase transitions to the third output phase. Specifically, based on the impedance Z reaching the switching value Zsw, the single outputting phase is switched to the simultaneous outputting phase.

The controller 21 judges whether the impedance Z decreases with time or increases with time, and detects the switching from the state in which the impedance Z decreases with time to the state in which the impedance Z increases with time. Thereby, the minimum value Zmin of the impedance Z can be detected. In addition, the switching value Zsw of the impedance Z is set to be identical to the minimum value Zmin or to be slightly greater than the minimum value Zmin. When the switching value Zsw is set to be identical to the minimum value Zmin, the controller 21 judges that the impedance Z reached the switching value Zsw at a time point when the impedance Z reached the minimum value Zmin or immediately thereafter. On the other hand, when the switching value Zsw is set to be slightly greater than the minimum value Zmin, the controller 21 judges that the impedance Z reached the switching value Zsw at a time point when the impedance Z increased slightly from the minimum value Zmin or immediately thereafter. Here, an arrival time Δtjudge from the control start in the second output phase until the impedance Z reaches the switching value Zsw is defined. In the present embodiment, during the arrival time Δtjudge, the output control in the second output phase is continued. Based on the judgment that the impedance Z reached the switching value Zsw, the controller 21 detects the arrival time Δtjudge.

If a transition occurs to the third output phase, the first electric energy and second electric energy are simultaneously output. Then, as described above, the treated target is denatured due to both the high-frequency current and the treatment energy generated by the functioning element 36. In one example, until the impedance Z of the treated target reaches a threshold Zth (see FIG. 6) (i.e. when the impedance Z is less than the threshold Zth) in the third output phase, the controller 21 executes constant electric power control which keeps the output electric power P of the first electric energy constant with time at an electric power value Pconst. Then, after the impedance Z reached the threshold Zth in the third output phase (i.e. when the impedance Z is the threshold Zth or above), the controller 21 executes constant voltage control which keeps the output voltage V of the first electric energy constant with time at a voltage value Vconst. In the state in which the constant voltage control is being executed, the output electric power P decreases with time. Note that the threshold Zth is greater than the switching value Zsw. In addition, it is preferable that the threshold Zth is greater than the initial impedance Z0.

In another example, a target value Ztar(t) of the impedance Z at each time t in the third output phase is set based on the variation with time of the impedance Z in the single outputting phase (e.g. the initial impedance Z0 and arrival time Δtjudge). For example, the target value Ztar(t) of the impedance Z is set in such a state that the impedance Z linearly increases with time in the third output phase. In addition, the controller 21 controls the output of the first electric energy in the third output phase in such a state that the impedance Z varies along the target value Ztar(t), and the output electric power P, output current I and output voltage V are adjusted. For example, when the impedance Z(t) at time t is less than the target value Ztar(t), the output electric power P of the first electric energy is increased. Note that the control of the first electric energy in the third output phase is not limited to the above-described example.

In the third output phase (simultaneous outputting phase), the controller 21 controls the second electric energy, based on a determined (selected) control pattern X. In addition, in the third output phase, the controller 21 judges (specifies) the state of the treated target, such as the volume v of the treated target, and determines the control pattern X, based on at least one of the impedance Z of the treated target at a certain time point in the single outputting phase (first output phase and second output phase) and the variation with time of the impedance Z of the treated target in the single outputting phase. For example, the state of the treated target is judged and the control pattern X is determined, based on at least one of the initial impedance Z0 detected in the first output phase and the arrival time Δtjudge which corresponds to the duration of the second output phase. Note that the information relating to the impedance Z in the single outputting phase is not limited to the initial impedance Z0 and arrival time Δtjudge. For example, the state of the treated target may be judged and the control pattern X may be determined, based on at least one of the above-described minimum value Zmin, a decrease rate ξ of the impedance Z from the initial impedance Z0 to minimum value Zmin, and a total time (Δtref+Δtjudge) of the first output phase and second output phase, in place of or in addition to the initial impedance Z0 and arrival time Δtjudge.

FIG. 10A is a view for describing a process of determining the control pattern X of the output control of the second electric energy in the third output phase in each of one example and another example. In addition, FIG. 10B is a view for describing a process of determining the control pattern X of the output control of the second electric energy in the third output phase in still another example. Note that the method of determining (selecting) the control pattern X is not limited to the examples which are described with reference to FIG. 10A and FIG. 10B. In addition, in each of the examples below, one of control patterns X1 to X3 is selected based on the state of the treated target (the variation with time of the impedance in the single outputting phase). For example, the control pattern X2 is selected when it is judged that the volume v of the treated target is proper. The control pattern X1 is selected when it is judged that the volume v of the treated target is relatively small. The control pattern X3 is selected when it is judged that the volume v of the treated target is relatively large.

As illustrated in FIG. 10A, in one example, based on the initial impedance Z0, the state of the treated target (the volume v of the treated target) is judged, and the control pattern X is determined. In this case, the judgment is made by using a first reference value Za and a second reference value Zb which is less than the first reference value Za. When the initial impedance Z0 is greater than the first reference value Za, the controller 21 judges that the volume v of the treated target is relatively small, and controls the output of the second electric energy by the control pattern X1. In addition, when the initial impedance Z0 is greater than the second reference value Zb and is equal to or less than the first reference value Za, the controller 21 judges that the volume v of the treated target is proper, and controls the output of the second electric energy by the control pattern X2. Besides, when the initial impedance Z0 is equal to or less than the second reference value Zb, the controller 21 judges that the volume v of the treated target is relatively large, and controls the output of the second electric energy by the control pattern X3.

As illustrated in FIG. 10A, in another example, based on the arrival time Δtjudge of the impedance Z up to the switching value Zsw, the state of the treated target (the volume v of the treated target) is judged, and the control pattern X is determined. In this case, the judgment is made by using a first reference time Δta and a second reference time Δtb which is longer than the first reference time Δta. When the arrival time Δtjudge is shorter than the first reference time Δta, the controller 21 judges that the volume v of the treated target is relatively small, and controls the output of the second electric energy by the control pattern X1. In addition, when the arrival time Δtjudge is shorter than the second reference time Δtb and is equal to or greater than the first reference time Δta, the controller 21 judges that the volume v of the treated target is proper, and controls the output of the second electric energy by the control pattern X2. Besides, when the arrival time Δtjudge is equal to or greater than the second reference time Δtb, the controller 21 judges that the volume v of the treated target is relatively large, and controls the output of the second electric energy by the control pattern X3. For example, the first reference time Δta is 600 ms, and the second reference time Δtb is 1000 MS.

As illustrated in FIG. 10B, in still another example, based on both the initial impedance Z0 and the arrival time Δtjudge of the impedance Z up to the switching value Zsw, the state of the treated target (the volume v of the treated target) is judged, and the control pattern X is determined. In this case, the judgment is made by using a reference value Zc and a reference time Δtc. When the initial impedance Z0 is greater than the reference value Zc and the arrival time Δtjudge is shorter than the reference time Δtc, the controller 21 judges that the volume v of the treated target is relatively small, and controls the output of the second electric energy by the control pattern X1. In addition, when the initial impedance Z0 is equal to or less than the reference value Zc and the arrival time Δtjudge is shorter than the reference time Δtc, the controller 21 judges that the volume v of the treated target is proper, and controls the output of the second electric energy by the control pattern X2. Besides, when the arrival time Δtjudge is equal to or greater than the reference time Δtc, the controller 21 judges that the volume v of the treated target is relatively large, regardless of the initial impedance Z0, and controls the output of the second electric energy by the control pattern X3.

In the third output phase, the controller 21 determines a parameter relating to the treatment energy generated by the functioning element 36 and a duration Δtset of the third output phase (simultaneous outputting phase), based on at least one of the impedance Z at a certain time point in the single outputting phase and the variation with time of the impedance Z in the single outputting phase. The parameter relating to the treatment energy and the duration $\Delta$tset are set in accordance with the determined control pattern X of the output control of the second electric energy. Here, when the functioning element 36 is the heat generating body 36A, a temperature T or the like of the heat generating body 36A in the third output phase is set as the parameter relating to the treatment energy (heat energy). On the other hand, when the functioning element 36 is the ultrasonic transducer 36B, the amplitude U and vibration velocity v, etc. in the vibrating body 40 in the third output phase are set as the parameters relating to the treatment energy (vibration energy). In the third output phase, the controller 21 controls the output of the second electric energy, based on the determined control pattern X, the set parameter relating to the treatment energy, and the set duration $\Delta$tset of the third output phase.

FIG. 11 illustrates a relationship of the parameter relating to treatment energy and the duration $\Delta$tset of the third output phase relative to the control pattern X of the output control of the second electric energy in the third output phase, in each of one example and another example. Note that the control pattern X is determined as described above.

In one example illustrated in FIG. 11, the heat generating body 36A is provided as the functioning element 36. When the control pattern X1 is selected, constant temperature control to keep the temperature of the heat generating body 36A constant with time at a first set temperature T1 is executed with respect to the output of the second electric energy, and the third output phase is continued during a first set time $\Delta$t1. In addition, when the control pattern X2 is selected, constant temperature control to keep the temperature of the heat generating body 36A constant with time at a second set temperature T2 that is higher than the first set temperature T1 is executed, and the third output phase is continued during a second set time $\Delta$t2 that is longer than the first set time $\Delta$t1. Besides, when the control pattern X3 is selected, constant temperature control to keep the temperature of the heat generating body 36A constant with time at a third set temperature T3 that is higher than the second set temperature T2 is executed, and the third output phase is continued during a third set time $\Delta$t3 that is longer than the second set time $\Delta$t2.

If the output of the second electric energy increases, the heat energy (treatment energy) generated by the heat generating body 36A increases and the temperature T of the heat generating body 36A rises. Thus, in the output control by the control pattern X2, the second electric energy that is output becomes greater and the heat energy generated by the heat generating body 36A become greater than in the output control by the control pattern X1. Similarly, in the output control by the control pattern X3, the second electric energy that is output becomes greater and the heat energy generated by the heat generating body 36A becomes greater than in the output control by the control pattern X2. For example, the first set temperature T1 is 180° C., the second set temperature T2 is 200° C., the third set temperature T3 is 220° C., the first set time $\Delta$t1 is 2 s, the second set time $\Delta$t2 is 3 s, and the third set time $\Delta$t3 is 4 s.

In another example illustrated in FIG. 11, the ultrasonic transducer 36B is provided as the functioning element 36. When the control pattern X1 is selected, the second electric energy is output in a state to keep the amplitude U in the vibrating body 40 (end effector) constant with time at a first set amplitude U1, and the third output phase is continued during the first set time $\Delta$t1. Specifically, constant current control to keep the output current I' constant with time at a current value I'1 is executed during the first set time $\Delta$t1. In addition, when the control pattern X2 is selected, the second electric energy is output in a state to keep the amplitude in the vibrating body 40 constant with time at a second set amplitude U2 that is greater than the first set amplitude U1, and the third output phase is continued during the second set time $\Delta$t2 that is longer than the first set time $\Delta$t1. Specifically, constant current control to keep the output current I' constant with time at a current value I'2 that is greater than the current value I'1 is executed during the second set time $\Delta$t2. Besides, when the control pattern X3 is selected, the second electric energy is output in a state to keep the amplitude in the vibrating body 40 constant with time at a third set amplitude U3 that is greater than the second set amplitude U2, and the third output phase is continued during the third set time $\Delta$t3 that is longer than the second set time $\Delta$t2. Specifically, constant current control to keep the output current I' constant with time at a current value I'3 that is greater than the current value I'2 is executed during the third set time $\Delta$t3.

If the output of the second electric energy increases by increasing the output current I', the vibration energy (treatment energy) generated by the ultrasonic transducer 36B increases and the amplitude U in the vibrating body 14 increases. Thus, in the output control by the control pattern X2, the second electric energy that is output becomes greater and the vibration energy generated by the ultrasonic transducer 36B becomes greater than in the output control by the control pattern X1. Similarly, in the output control by the control pattern X3, the second electric energy that is output becomes greater and the vibration energy generated by the ultrasonic transducer 36B becomes greater than in the output control by the control pattern X2. For example, when the amplitude U is defined as an amplitude at a distal end of the vibrating body 40, the first set amplitude U1 is 40 μm, the second set amplitude U2 is 60 μm, and the third set amplitude U3 is 180 μm. Also in the case in which set vibration velocities v1, v2 and v3 (v1<v2<v3) are set in place of the set amplitudes U1, U2 and U3, the same description as when the set amplitudes U1, U2 and U3 are set is applicable.

As described above, in the present embodiment, the duration $\Delta$tset of the simultaneous outputting phase (third output phase) is adjusted in accordance with the variation with time of the impedance Z in the single outputting phase. In addition, in accordance with the variation with time of the impedance Z in the single outputting phase, the magnitude of the second electric energy, which is output from the second energy output section 26, is adjusted, and the magnitude of the treatment energy (heat energy or vibration energy, etc.) generated by the functioning element 36 is adjusted.

In addition, in the example in which the control pattern X in the third output phase is determined based on the initial impedance Z0, when the initial impedance Z0 is equal to or less than the reference value (e.g. Za; Zb; Zc), the duration $\Delta$tset of the third output phase becomes longer than when the initial impedance Z0 is greater than the reference value (e.g. Za; Zb; Zc). Besides, when the initial impedance Z0 is equal to or less than the reference value (e.g. Za; Zb; Zc), the second electric energy that is output in the third output phase becomes greater and the treatment energy (heat energy or vibration energy, etc.) generated by the functioning element 36 in the simultaneous outputting phase becomes greater than when the initial impedance Z0 is greater than the reference value (e.g. Za; Zb; Zc).

Furthermore, in the example in which the control pattern X in the third output phase is determined based on the arrival time Δtjudge of the impedance Z up to the switching value Zsw, when the arrival time Δtjudge is equal to or longer than the reference time (e.g. Δta; Δtb; Δtc), the duration Δtset of the third output phase becomes longer than when the arrival time Δtjudge is shorter than the reference time (e.g. Δta; Δtb; Δtc). In addition, when the arrival time Δtjudge is equal to or longer than the reference time (e.g. Δta; Δtb; Δtc), the second electric energy that is output in the third output phase becomes greater and the treatment energy (heat energy or vibration energy, etc.) generated by the functioning element 36 in the simultaneous outputting phase becomes greater than when the arrival time Δtjudge is shorter than the reference time (e.g. Δta; Δtb; Δtc).

Figure 12:
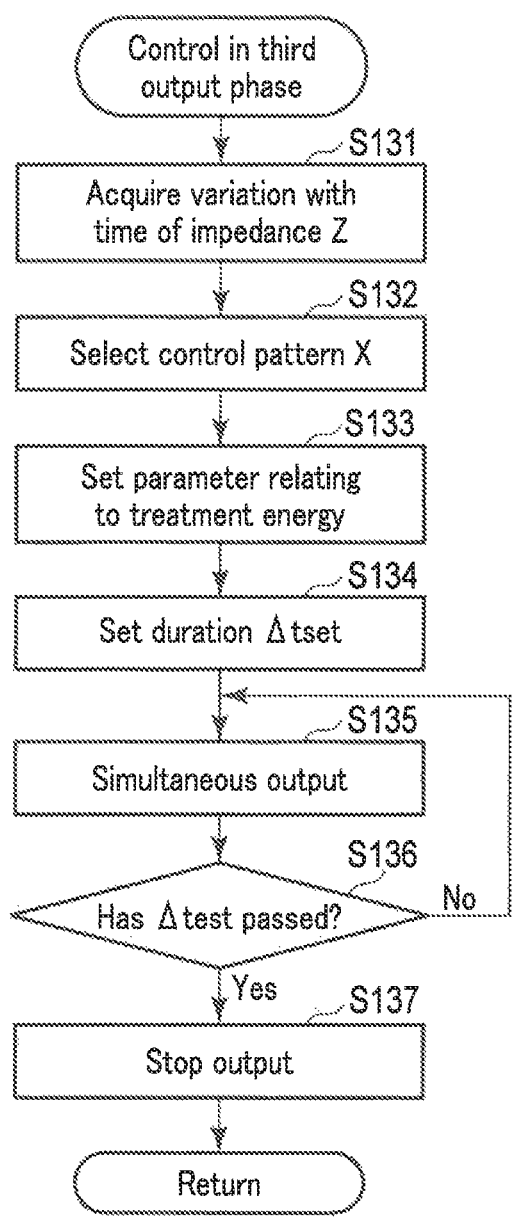
FIG. 12 is a flowchart illustrating a process which the controller according to the first embodiment executes in the control in the third output phase.

FIG. 12 is a flowchart illustrating a process which is executed by the controller 21 in the control in the third output phase. As illustrated in FIG. 12, in the control in the third output phase, the controller 21 acquires the variation with time of the impedance Z of the treated target in the single outputting phase (first output phase and second output phase) (step S131). At this time, the initial impedance Z0 and the arrival time Δtjudge of the impedance Z up to the switching value Zsw, etc. are acquired. Then, based on the information relating to the variation with time of the impedance Z in the single outputting phase, the controller 21 judges the state of the treated target such as the volume v of the treated target, and determines the control pattern X of the output control of the second electric energy in the third output phase (step S132). At this time, for example, like any one of the above-described examples, the control pattern X is selected. Then, in accordance with the determined control pattern X, the controller 21 sets the parameter (temperature T or amplitude U, etc.) relating to the treatment energy generated by the functioning element 36 (step S133) and sets the duration Δtset of the third output phase (step S134). At this time, for example, like any one of the above-described examples, the parameter relating to the treatment energy and the duration Δtset are set.

Then, based on the determined control pattern X, the set parameter relating to the treatment energy, and the set duration Δtset, the controller 21 causes the first electric energy and second electric energy to be simultaneously output (step S135). Thereby, the treated target is denatured due to both the high-frequency current and the treatment energy generated by the functioning element 36. At this time, for example, like any one of the above-described examples, the output control of the first electric energy and second electric energy is executed. Further, the controller 21 judges whether the set duration Δtset has passed since the control start in the third output phase (step S136). If the set duration Δtset has not passed (step S136—No), the process returns to step S135, and the simultaneous output of the first electric energy and second electric energy is continued. If the set duration Δtset has passed (step S136—Yes), the simultaneous output of the first electric energy and second electric energy is stopped (step S137), and the control in the third output phase is finished.

In the present embodiment, by the controller 21 executing the control as described above, the parameter (temperature T or amplitude U, etc.) relating to the treatment energy in the simultaneous outputting phase and the duration Δtset of the simultaneous outputting phase are set based on the variation with time of the impedance Z of the treated target in the single outputting phase (e.g. the initial impedance Z0 and arrival time Δtjudge, etc.). In addition, based on the set parameter and duration Δtset, the output of the second electric energy in the simultaneous outputting phase (third output phase) is controlled. Since the parameter relating to the treatment energy and the duration Δtset are set based on the impedance Z of the treated target, the parameter relating to the treatment energy and the duration Δtset are set in accordance with the state of the treated target such as the volume v of the treated target. In addition, since the output of the second electric energy is controlled based on the parameter and duration Δtset which are set in accordance with the state of the treated target, the treatment energy (heat or ultrasonic vibration, etc.) is properly generated by the functioning element 36 in accordance with the state of the treated target such as the volume v of the treated target. Thereby, in the simultaneous outputting phase, the treatment energy generated by the functioning element 36 is properly applied to the treated target in accordance with the state of the treated target.

In addition, in the present embodiment, the duration Δtset of the third output phase is properly set in accordance with the state of the treated target. Thus, in the third output phase, the high-frequency current and the treatment energy generated by the functioning element 36 are applied to the treated target for only a proper time, in accordance with the state of the treated target such as the volume v of the treated target.

As described above, in the present embodiment, since the high-frequency current and the treatment energy (heat or vibration, etc.) are properly applied to the treated target in accordance with the state of the treated target, it is possible to effectively prevent an invasion to a part of the biological tissue other than the treated target by the heat generated due to the high-frequency current and treatment energy. In particular, it is possible to effectively prevent an invasion (thermal side spread) by the heat due to the high-frequency current and treatment energy from the treated target to a part other than the treated target in the width direction of the end effector 7. In the present embodiment, since the high-frequency current and treatment energy (heat or vibration, etc.) are applied to the treated target in accordance with the state of the treated target, A VBP (Vessel Burst Pressure) of a sealed part of the treated target (blood vessel) has a high value after the end of the third output phase. Accordingly, the treated target is exactly sealed by the treatment which is performed through the first output phase to the third output phase. Incidentally, the VBP is a pressure under which the sealed part is peeled when a water pressure is applied to the sealed part of the treated target after the end of the treatment (after the end of the third output phase).

(Modifications)

Note that the method of setting the parameter relating to the treatment energy and the duration Δtset of the third output phase is not limited to the method (see FIG. 11) described in the first embodiment. In a first modification illustrated in FIG. 13, in the third output phase (simultaneous outputting phase), the controller 21 controls the output of the second electric energy from the second energy output section 26, thereby increasing with time the treatment energy which is generated by the functioning element 36 in the third output phase. Thereby, in the example in which the functioning element 36 is the heat generating body 36A, the temperature T of the heat generating body 36A increases with time (linearly) from an initial temperature T0 in the third output phase. In addition, in the example in which the functioning element 36 is the ultrasonic transducer 36B, the amplitude U of the vibrating body 40 increases with time (linearly) from an initial amplitude U0 in the third output phase.

In the present modification, the length of the duration Δtset of the simultaneous outputting phase is adjusted based on at least one of the impedance Z at a certain time point in the single outputting phase and the variation with time of the impedance Z of the treated target in the single outputting phase. For example, when the output control of the second electric energy is executed by the control pattern X1, the third output phase is continued for the first set time Δt1. When the output control of the second electric energy is executed by the control pattern X2, the third output phase is continued for the second set time Δt2 which is longer than the first set time Δt1. When the output control of the second electric energy is executed by the control pattern X3, the third output phase is continued for the third set time Δt3 which is longer than the second set time Δt2.

In the present modification, by the length of the duration Δtset of the third output phase being adjusted as described above, the magnitude of the treatment energy at the time of the end of the third output phase (simultaneous outputting phase) is adjusted. Thereby, in the example in which the functioning element 36 is the heat generating body 36A, when the output control of the second electric energy is executed by the control pattern X1, the temperature T of the heat generating body 36A rises from the initial temperature T0 up to a first end temperature T1 at the time of the end of the third output phase. In addition, when the output control is executed by the control pattern X2, the temperature T of the heat generating body 36A rises up to a second temperature T2 that is higher than the first end temperature T1 at the time of the end of the third output phase. When the output control is executed by the control pattern X3, the temperature T of the heat generating body 36A rises up to a third temperature T3 that is higher than the second end temperature T2 at the time of the end of the third output phase.

Figure 13:
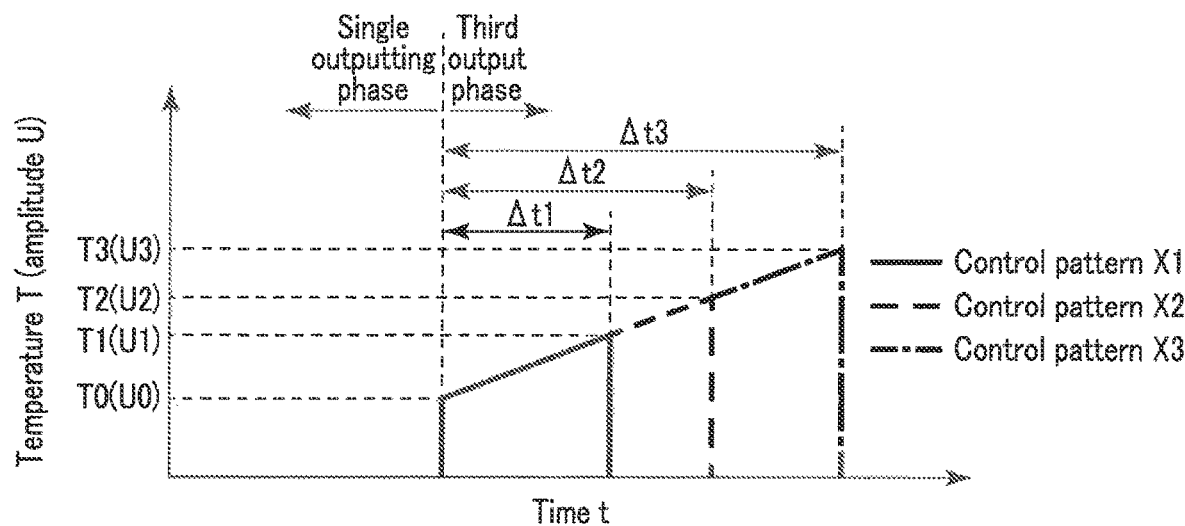
FIG. 13 is a schematic view illustrating a relationship, in a first modification, of the parameter relating to treatment energy and the duration of the third output phase relative to the control pattern of the output control of the second electric energy in the third output phase.

Note that, in this modification, no matter which of the control patterns X is selected, an increase rate ε with time of the temperature T is identical. Also in the example in which the functioning element 36 is the ultrasonic transducer 36B, the initial amplitude U0 and end amplitudes U1, U2 and U3 (U0<U1<U2<U3) are used or the initial vibration velocity v0 and end vibration velocities v1, v2 and v3 (v0<v1<v2<v3) are used in place of the initial temperature T0 and end temperatures T1, T2 and T2. Thereby, the same description as in the example in which the functioning element 36 is the heat generating body 36A is applicable. In FIG. 13, a variation with time of the temperature of the heat generating body 36A (the amplitude U of the vibrating body 40) in the third output phase is indicated by a solid line when the output control is executed by the control pattern X1, is indicated by a broken line when the output control is executed by the control pattern X2, and is indicated by a dot-and-dash line when the output control is executed by the control pattern X3.

Figure 14:
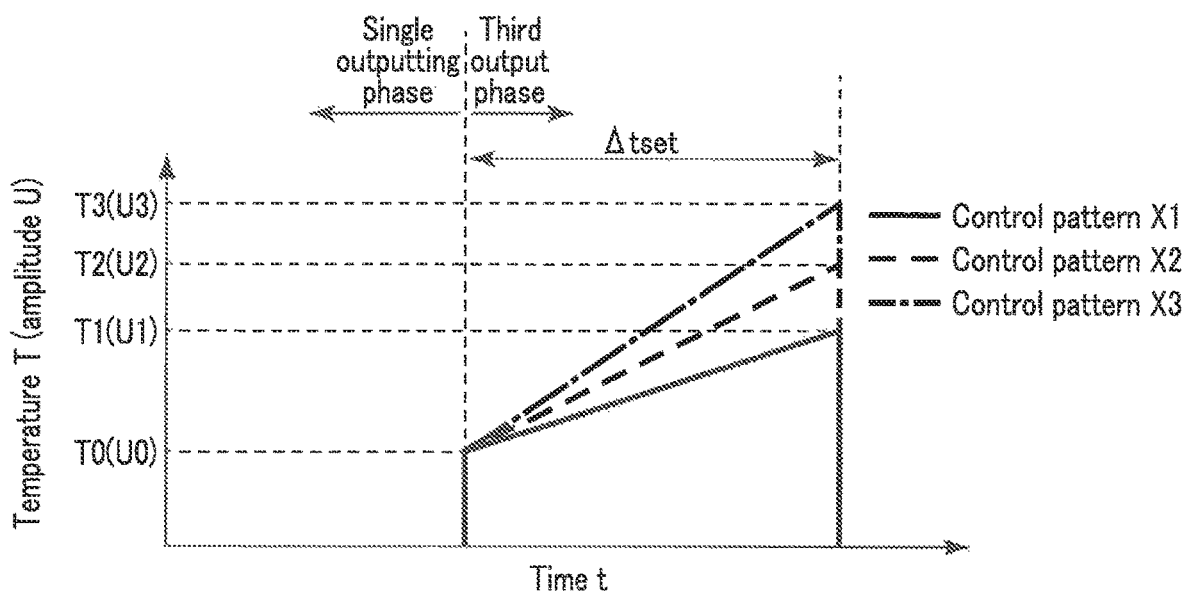
FIG. 14 is a schematic view illustrating a relationship, in a second modification, of the parameter relating to treatment energy and the duration of the third output phase relative to the control pattern of the output control of the second electric energy in the third output phase.

In a second modification illustrated in FIG. 14, too, in the third output phase (simultaneous outputting phase), the controller 21 controls the output of the second electric energy from the second energy output section 26, thereby increasing with time the treatment energy which is generated by the functioning element 36 in the third output phase. However, in this modification, the increase rate with time of the treatment energy generated by the functioning element 36 in the simultaneous outputting phase is adjusted in accordance with the variation with time of the impedance Z in the single outputting phase. For example, when the output control is executed by the control pattern X2, the increase rate with time of the treatment energy becomes greater than when the output control is executed by the control pattern X1. In addition, when the output control is executed by the control pattern X3, the increase rate with time of the treatment energy becomes greater than when the output control is executed by the control pattern X2.

Here, in the example in which the control pattern X in the third output phase is determined based on the initial impedance Z0, when the initial impedance Z0 is equal to or less than the reference value (e.g. Za; Zb; Zc), the increase rate with time of the treatment energy (heat energy or vibration energy, etc.) in the third output phase becomes greater than when the initial impedance Z0 is greater than the reference value (e.g. Za; Zb; Zc). In addition, in the example in which the control pattern X in the third output phase is determined based on the arrival time Δtjudge of the impedance Z up to the switching value Zsw, when the arrival time Δtjudge is equal to or greater than the reference time (e.g. Δta; Δtb; Δtc), the increase rate with time of the treatment energy in the third output phase becomes greater than when the arrival time Δtjudge is shorter than the reference time (e.g. Δta; Δtb; Δtc).

In the present modification, by the increase rate with time of the treatment energy in the third output phase being adjusted as described above, the magnitude of the treatment energy at the time of the end of the third output phase (simultaneous outputting phase) is adjusted. For example, in the example in which the functioning element 36 is the heat generating body 36A, when the output control of the second electric energy is executed by the control pattern X1, the temperature T of the heat generating body 36A increases with time from the initial temperature T0 at a first set increase rate ε1 in the third output phase, and the temperature T of the heat generating body 36A rises up to the first end temperature T1 at the time of the end of the third output phase. In addition, when the output control of the second electric energy is executed by the control pattern X2, the temperature T of the heat generating body 36A increases with time at a second set increase rate ε2 that is greater than the first set increase rate ε1 in the third output phase, and the temperature T of the heat generating body 36A rises up to the second end temperature T2 that is higher than the first end temperature T1 at the time of the end of the third output phase. Besides, when the output control of the second electric energy is executed by the control pattern X3, the temperature T of the heat generating body 36A increases with time at a third set increase rate ε3 that is greater than the second set increase rate ε2 in the third output phase, and the temperature T of the heat generating body 36A rises up to the third end temperature T3 that is higher than the second end temperature T2 at the time of the end of the third output phase.

In the present modification, no matter which of the control patterns X is selected, the length of the duration Δtset of the third output mode and the magnitude of the treatment energy (the initial temperature T0) at the time of the control start in the third output phase are identical. Also in the example in which the functioning element 36 is the ultrasonic transducer 36B, the initial amplitude U0 and end amplitudes U1, U2 and U3 (U0<U1<U2<U3) are used or the initial vibration velocity v0 and end vibration velocities v1, v2 and v3 (v0<v1<v2<v3) are used in place of the initial temperature T0 and end temperatures T1, T2 and T2. Thereby, the same description as in the example in which the functioning element 36 is the heat generating body 36A is applicable. In FIG. 14, a variation with time of the temperature of the heat generating body 36A (the amplitude U of the vibrating body 40) in the third output phase is indicated by a solid line when the output control is executed by the control pattern X1, is indicated by a broken line when the output control is executed by the control pattern X2, and is indicated by a dot-and-dash line when the output control is executed by the control pattern X3.

In addition, in the above-described embodiment, etc., in the third output phase, the output control of the second electric energy is executed based on any one of the three control patterns X1 to X3, but the embodiment, etc. are not limited to this. In the third output phase, the output of the second electric energy may be executed based on any one of plural control patterns X, on the basis of at least one of the impedance Z at a certain time point in the single outputting phase and the variation with time of the impedance Z in the single outputting phase. Specifically, the number of control patterns X of the output control of the second electric energy in the third output phase may be two or four, if the control patterns X are classified into a plurality of control patterns X.

Figure 15:
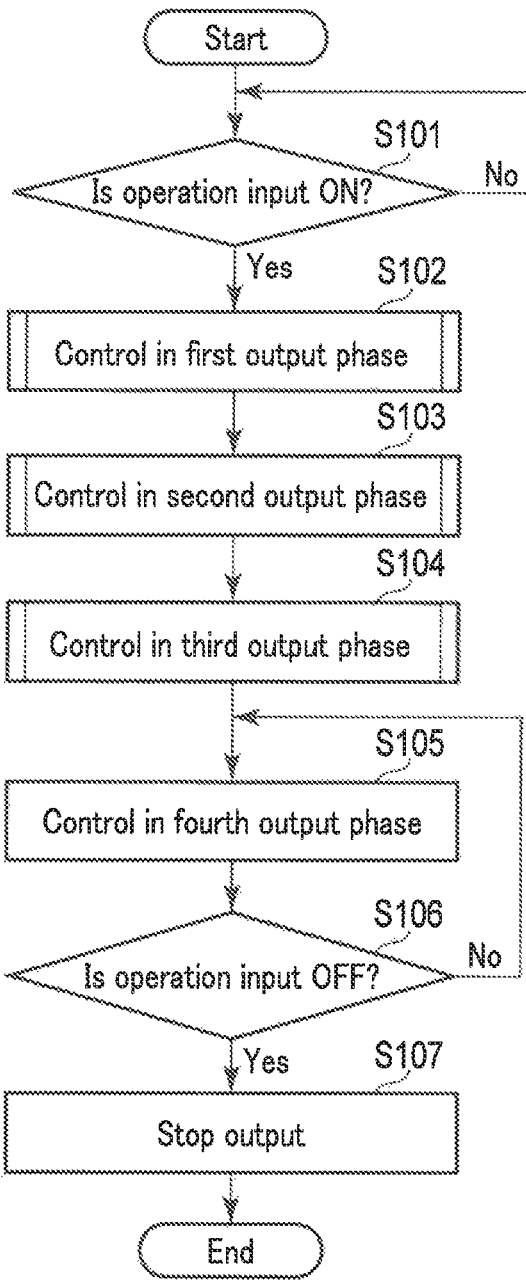
FIG. 15 is a flowchart illustrating a process in a treatment, which is executed by the controller of an energy control device according to a third modification.

Moreover, in the above-described embodiment, etc., after the third output phase is continued for the set duration Δtset, the controller 21 stops the output of the first electric energy and second electric energy, but the embodiment, etc. are not limited to this. For example, as illustrated in FIG. 15 as a third modification, after the end of the control (step S104) in the third output phase, the controller 21 executes control in a fourth output phase (step S105). In this modification, the process of step S137 is not executed in the control in the third output phase, and the third output phase transitions to the fourth output phase.

In the fourth output phase, by the output control by the controller 21, at least one of the first electric energy and second electric energy is output in such a state that the treated target is not denatured due to each of the high-frequency current and the treatment energy (heat or ultrasonic vibration, etc.). For example, in the fourth output phase, even if the first electric energy is output, the first electric energy is so small that the treated target is not denatured due to the high-frequency current, or the first electric energy is intermittently output for only a small time so that the treated target is not denatured due to the high-frequency current. Similarly, in the fourth output phase, even if the second electric energy is output, the second electric energy is so small that the treated target is not denatured due to the treatment energy, or the second electric energy is intermittently output for only a small time so that the treated target is not denatured due to the treatment energy.

As long as the operation input by the operation button 18 is kept in the ON state (step S106—No), the controller 21 continues the output control in the fourth output phase. In addition, based on the switching of the operation input to the OFF state (step S106—Yes), the controller 21 stops the output of the first electric energy and second electric energy (step S107). Note that, instead of the process of step S106, the controller 21 may stop the output of the first electric energy and second electric energy, based on the passage of a specified time Δtstop from the start of the fourth output phase (the end of the third output phase).

In addition, in the above-described embodiment, etc., the controller 21 starts the output of the second electric energy after the impedance Z reaches the minimum value Zmin, but the embodiment, etc. are not limited to this. For example, as illustrated in FIG. 16 to FIG. 19 as a fourth modification, the output of the second electric energy may be started before the impedance Z reaches the minimum value Zmin. In this modification, as illustrated in FIG. 16, after the end of the control in the second output phase (step S103), the controller 21 executes control (step S108) in a relay output phase. Then, after the end of the control (step S108) in the relay output phase, the controller 21 executes the control in the third output phase (step S104). Furthermore, in this modification, the first output phase and second output phase become a single outputting phase in which only the first electric energy is output and the second electric energy is not output from the second energy output section 26. Besides, the relay output phase and third output phase become a simultaneous outputting phase in which both the first electric energy and the second electric energy are simultaneously output.

Figure 17:
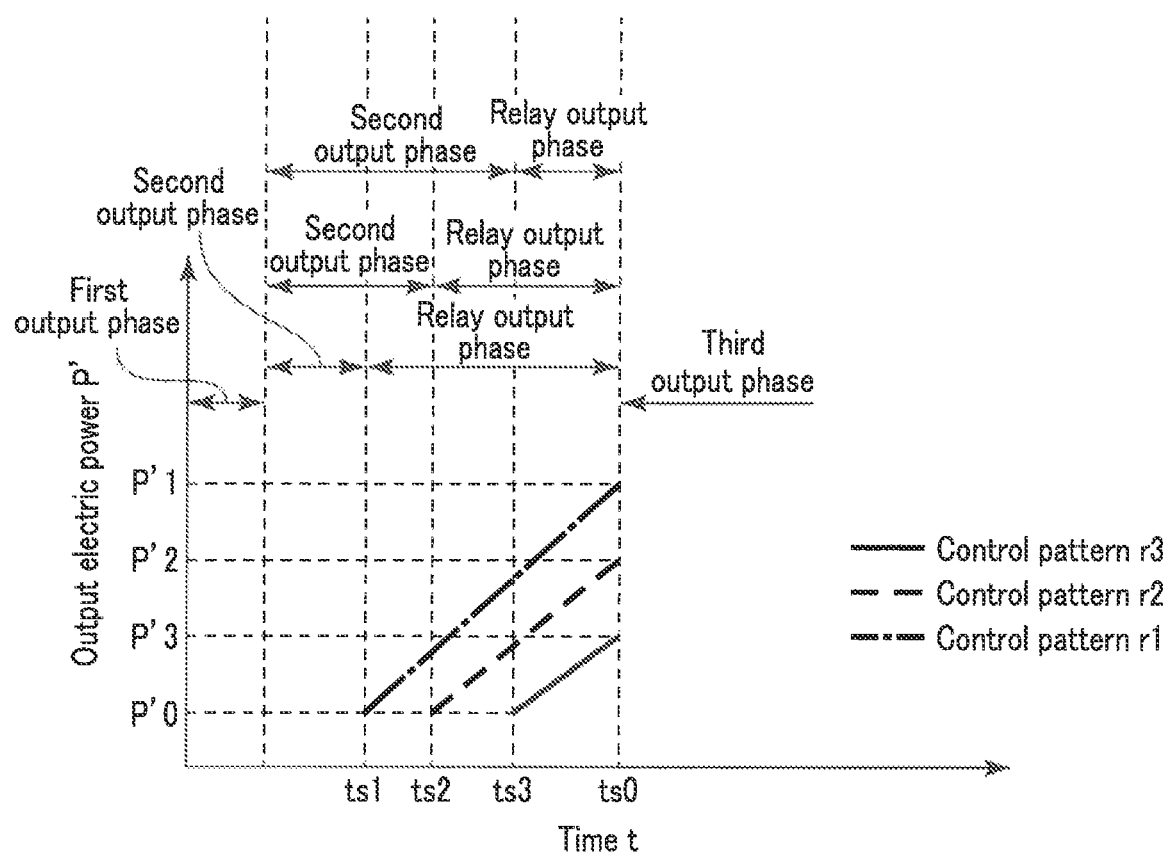
FIG. 17 is a schematic view illustrating an example of a variation with time of output electric power of the second electric energy in a relay output phase in the treatment using the energy control device according to the fourth modification.

In this modification, based on the initial impedance Z0 detected in the first output phase, the controller 21 controls the timing of starting the output of the second electric energy (i.e. the timing of switching the second output phase to the relay output phase). FIG. 17 is a view illustrating an example of a variation with time of output electric power P' of the second electric energy in the relay output phase. In FIG. 17, the abscissa axis indicates time t with reference to the control start in the first output phase (the output start of the first electric energy), and the ordinate axis indicates the output power P'.

As illustrated in FIG. 17, in one example of this modification, based on the initial impedance Z0, a control pattern r (r1, r2, r3) relating to the output control of the second electric energy in the relay output phase is determined. Then, in the relay output phase, the output of the second electric energy is controlled in accordance with the determined control pattern r. For example, when the output control of the second electric energy is executed by the control pattern r1, the output of the second electric energy begins, based on the reaching to time ts1 after the first output phase was switched to the second output phase. Specifically, based on the reaching to time ts1, the single outputting phase (second output phase) in which only the first electric energy is output is switched to the simultaneous outputting phase (relay output phase) in which the first electric energy and second electric energy are simultaneously output. In the control pattern r1, the relay output phase continues from time ts1 to time ts0, and the output power P' increases with time from P'0 to P'1 during the relay output phase.

When the output control of the second electric energy is executed by the control pattern r2, the output of the second electric energy begins, based on the reaching to time ts2 which is later than the time ts1, and switching occurs to the relay output phase. Then, the relay output phase continues from time ts2 to time ts0, and the output power P' increases with time from P'0 to P'2, which is less than P'1, during the relay output phase. Thus, when the output control of the second electric energy is executed by the control pattern r2, the time of the second output phase (single outputting phase) becomes longer and the time of the relay output phase becomes shorter than when the output control of the second electric energy is executed by the control pattern r1. Besides, when the output control of the second electric energy is executed by the control pattern r3, the output of the second electric energy begins, based on the reaching to time ts3, which is later than the time ts2, and switching occurs to the relay output phase. Then, the relay output phase continues from time ts3 to time ts0, and the output power P' increases with time from P'0 to P'3, which is less than P'2, during the relay output phase. Thus, when the output control of the second electric energy is executed by the control pattern r3, the time of the second output phase (single outputting phase) becomes longer and the time of the relay output phase becomes shorter than when the output control of the second electric energy is executed by the control pattern r2.

In FIG. 17, the variation with time of the output electric power P' of the second electric power in the relay output phase is indicated by a dot-and-dash line when the output control is executed by the control pattern r1, is indicated by a broken line when the output control is executed by the control pattern r2, and is indicated by a solid line when the output control is executed by the control pattern r3. In addition, the time ts1, time ts2 and time ts3 are before the impedance Z reaches the minimum value Zmin, and the time ts0 is after the impedance Z reaches the minimum value Zmin.

Here, for example, when the treated target is a blood vessel which is thin (small in volume v), there are a less number of paths of flow of electric current than in the case of a thick blood vessel, and the amount of moisture included in the treated target becomes smaller, and it is thus relatively difficult for a high-frequency current to flow through the treated target. Hence, the initial impedance Z0 detected in the first output phase becomes higher than in the case of the thick blood vessel. In this case, the output control of the second electric energy is executed by the control pattern r (e.g. control pattern r3) in which the timing of starting the output of the second electric energy (the timing of switching from the second output phase to the relay output phase) is later. On the other hand, for example, when the treated target is a blood vessel which is thick (large in volume v), there are a greater number of paths of flow of electric current than in the case of a thin blood vessel, and the amount of moisture included in the treated target becomes larger, and it is thus relatively easy for a high-frequency current to flow through the treated target. Hence, the detected initial impedance Z0 becomes lower than in the case of the thin blood vessel. In this case, the output control of the first electric energy is executed by the control pattern r (e.g. control pattern r1) in which the timing of the start of the output of the second electric energy is earlier.

Figure 18:
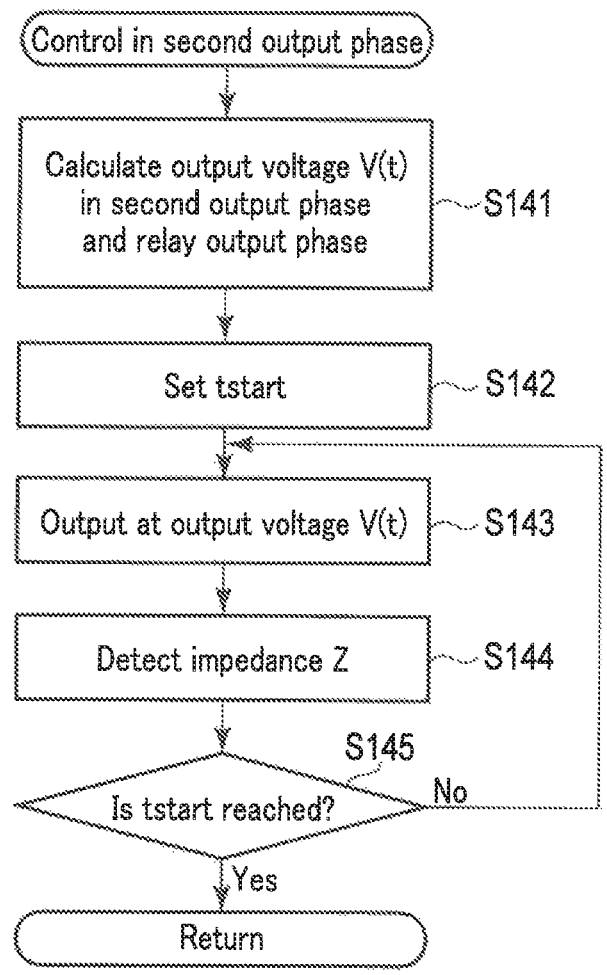
FIG. 18 is a flowchart illustrating a process which the controller according to the fourth modification executes in the control in the second output phase.

FIG. 18 is a flowchart illustrating a process which is executed by the controller 21 of the present modification in the control in the second output phase. FIG. 19 is a flowchart illustrating a process which is executed by the controller 21 of this modification in the control in the relay output phase. Here, a description is given of an example in which the output control to linearly increase with time the output voltage V(t) of the first electric energy is executed from the start of the second output phase to the end of the relay output phase. As illustrated in FIG. 18, in the control in the second output phase, the controller 21 calculates the output voltage V(t) at each time t in the second output phase and the relay output phase, based on the initial impedance Z0 detected in the first output phase (step S141). At this time, based on the initial impedance Z0, the controller 21 calculates the output voltage V(t) by determining the control pattern (e.g. Y) of the first electric energy and the increase rate α with time of the output voltage V(t) in the second output phase and relay output phase. In addition, based on the initial impedance Z0, the controller 21 sets a start time tstart of starting the output of the second electric energy (step S142). Note that the start time tstart is, for example, the above-described ts1, ts2 or ts2, and the start time tstart is set to be earlier than the time at which the impedance Z reaches the minimum value Vmin. In addition, the controller 21 causes the first energy output section 25 to output the first electric energy at the output voltage V(t) corresponding to time t (step S143). Further, the controller 21 detects the impedance Z of the treated target, based on the output current I and output voltage V (step S144).

Then, the controller 21 judges whether the time t reached the set start time tstart (step S145). If the time t does not reach the start time tstart (step S145—No), the process returns to step S143, and the output of the first electric energy at the output voltage V(t) (step S143) and the detection of the impedance Z (step S144) are repeated. If the time t reached the start time tstart (step S145—Yes), the control in the second output phase (single outputting phase) ends, and a transition occurs to the relay output phase (simultaneous outputting phase).

As illustrated in FIG. 19, in the control in the relay output phase, the controller 21 selects the control pattern r of the output control of the second electric energy in the relay output phase, based on the start time tstart (step S151). Then, the controller 21 causes the first energy output section 25 to output the first electric energy at the output voltage V(t) corresponding to time t, which was calculated in step S141 (step S152). In addition, the controller 21 causes the second energy output section 26 to output the second electric energy in accordance with the control pattern r selected in step S151 (step S153). Further, the controller 21 detects the impedance Z of the treated target, based on the output current I and output voltage V (step S154).

Then, the controller 21 judges whether the impedance Z of the treated target reached the minimum value Zmin (step S155). After the impedance Z of the treated target reached the minimum value Zmin (step S155—Yes), the controller 21 judges whether the impedance Z reached the switching value Zsw (step S156). If the impedance Z does not reach the minimum value Zmin (step S155—No), or if the impedance Z does not reach the switching value Zsw (step S156—No), the process returns to step S152, and the output of the first electric energy at the output voltage V(t) (step S152), the output of the second electric energy corresponding to the control pattern r (step S153) and the detection of the impedance Z (step S154) are repeated. If the impedance Z reached the switching value Zsw (step S156—Yes), the control in the relay output phase ends, and a transition occurs to the third output phase.

In the above-described embodiment, etc., the end effector 7 includes the paired grasping pieces 15 and 16, but the embodiment, etc. are not limited to this. For example, the above-described control may be applied to a configuration in which a high-frequency current is passed through the treated target between an electrode provided in the end effector (7) and a counter-electrode plate disposed on the outside of the body. In this case, for example, the end effector (7) is formed in a hook shape or a spatula shape, and ultrasonic vibration generated by the ultrasonic transducer (36B) that is the functioning element (36) is transmitted to the end effector (7) as treatment energy.

In the above-described embodiment, etc., the controller (21) executes continuing, from the output start, the single outputting phase in which only the first electric energy is supplied to the electrode (31, 32); transitioning the single outputting phase to the simultaneous outputting phase in which the first electric energy and the second electric energy are simultaneously output and the treated target is denatured due to both of the high-frequency current and the treatment energy generated by the functioning element (36); and detecting the impedance (Z) of the treated target with time in the single outputting phase. In addition, the controller (21) sets the parameter (temperature T or amplitude U, etc.) relating to the treatment energy in the simultaneous outputting phase and the duration (Δtset) of the simultaneous outputting phase, based on at least one of the impedance (Z) at a certain time point in the single outputting phase and the variation with time of the impedance (Z) in the single outputting phase, and controls the output of the second electric energy in the simultaneous outputting phase, based on the parameter and duration (Δtset) which are set.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. An energy control device configured to control supply of energy to an energy treatment instrument, the energy treatment instrument including an electrode and a functioning element, the energy control device comprising:
   a first energy output source configured to output first electric energy, and configured to pass a high-frequency current through a treated target by supplying the output first electric energy to the electrode;
   a second energy output source configured to output second electric energy different from the first electric energy, and configured to generate treatment energy different from the high-frequency current in the functioning element by supplying the output second electric energy to the functioning element; and
   a controller configured to control an output of the first electric energy from the first energy output source and an output of the second electric energy from the second energy output source,
   the controller being configured to execute:
   carrying out a single outputting phase in which only the first electric energy is output;
   detecting an impedance of the treated target with time in the single outputting phase;
   transitioning the single outputting phase to a simultaneous outputting phase in which the first electric energy and the second electric energy are simultaneously output and the treated target is denatured due to both of the high-frequency current and the treatment energy; and
   setting a control pattern relating to the treatment energy in the simultaneous outputting phase, based on at least one of the impedance at a certain time point in the single outputting phase and a variation with time of the impedance in the single outputting phase, and controlling the output of the second electric energy in the simultaneous outputting phase, based on the set control pattern.

2. The energy control device of claim 1, wherein the controller is configured to set, as the control pattern, at least one of a parameter relating to the treatment energy in the simultaneous outputting phase and a duration of the simultaneous outputting phase.

3. The energy control device of claim 2, wherein the controller is configured to adjust a length of the duration of the simultaneous outputting phase in accordance with at least one of the impedance at the certain time point in the single outputting phase and the variation with time of the impedance in the single outputting phase.

4. The energy control device of claim 3, wherein the controller is configured to control the output of the second electric energy from the second energy output source in the simultaneous outputting phase, thereby increasing with time the treatment energy generated in the functioning element in the simultaneous outputting phase, and the controller is configured to adjust the length of the duration of the simultaneous outputting phase, thereby adjusting a magnitude of the treatment energy at a time of an end of the simultaneous outputting phase.

5. The energy control device of claim 2, wherein the controller is configured to adjust a magnitude of the treatment energy generated by the functioning element in the simultaneous outputting phase in accordance with at least one of the impedance at the certain time point in the single outputting phase and the variation with time of the impedance in the single outputting phase.

6. The energy control device of claim 5, wherein the controller is configured to control the output of the second electric energy from the second energy output source in the simultaneous outputting phase, thereby increasing with time the treatment energy generated in the functioning element in the simultaneous outputting phase, and the controller is configured to adjust an increase rate with time of the treatment energy in the simultaneous outputting phase in accordance with at least one of the impedance at the certain time point in the single outputting phase and the variation with time of the impedance in the single outputting phase, thereby adjusting the magnitude of the treatment energy at a time of an end of the simultaneous outputting phase.

7. The energy control device of claim 1, wherein the controller is configured to transition the single outputting phase to the simultaneous outputting phase, based on reaching of the impedance to a switching value after the impedance reaches a minimum value in the single outputting phase.

8. The energy control device of claim 7, wherein the controller is configured to set, as the control pattern, at least one of a parameter relating to the treatment energy in the simultaneous outputting phase and a duration of the simultaneous outputting phase.

9. The energy control device of claim 8, wherein the controller is configured to execute, in the single outputting phase, at least one of detection of an initial impedance which is the impedance at an output start time or immediately thereafter, and detection of an arrival time until the impedance reaches the switching value, and
   the controller is configured to set the parameter relating to the treatment energy in the simultaneous outputting phase and the duration of the simultaneous outputting phase, based on at least one of the detected initial impedance and the detected arrival time.

10. The energy control device of claim 9, wherein the controller is configured to execute at least one of:
    setting the duration of the simultaneous outputting phase to be longer when the initial impedance is equal to or less than a reference value than when the initial impedance is greater than the reference value; and
    setting the duration of the simultaneous outputting phase to be longer when the arrival time up to the switching value is equal to or longer than a reference time than when the arrival time up to the switching value is shorter than the reference time.

11. The energy control device of claim 9, wherein the controller is configured to execute at least one of:
    setting the treatment energy generated by the functioning element in the simultaneous outputting phase to be greater when the initial impedance is equal to or less than a reference value than when the initial impedance is greater than the reference value; and
    setting the treatment energy generated by the functioning element in the simultaneous outputting phase to be greater when the arrival time up to the switching value is equal to or longer than a reference time than when the arrival time up to the switching value is shorter than the reference time.

12. The energy control device of claim 9, wherein the controller is configured to control the output of the second electric energy from the second energy output source in the simultaneous outputting phase, thereby increasing with time the treatment energy generated by the functioning element in the simultaneous outputting phase, and the controller is configured to execute at least one of:
setting an increase rate with time of the treatment energy in the simultaneous outputting phase to be greater when the initial impedance is equal to or less than a reference value than when the initial impedance is greater than the reference value; and
setting the increase rate with time of the treatment energy in the simultaneous outputting phase to be greater when the arrival time up to the switching value is equal to or longer than a reference time than when the arrival time up to the switching value is shorter than the reference time.

13. The energy control device of claim 1, wherein, after continuing the simultaneous outputting phase for the set duration, the controller is configured to stop the output of the first electric energy and the second electric energy, or configured to make a transition to a phase in which at least one of the first electric energy and the second electric energy is output so that the treated target is not denatured due to each of the high-frequency current and the treatment energy.

14. The energy control device of claim 1, wherein the controller is configured to execute, as the single outputting phase, a first output phase in which constant electric power control to keep an output electric power of the first electric energy constant with time is executed, and a second output phase in which control to increase with time the output of the first electric energy is executed.

15. The energy control device of claim 14, wherein the controller is configured to execute, in the first output phase, detecting an initial impedance of the treated target, and configured to execute, in the second output phase, controlling the output of the first electric energy, based on the initial impedance.

16. The energy control device of claim 15, wherein the controller is configured to adjust an increase rate with time of the first electric energy in the second output phase.

17. A treatment system comprising:
the energy control device of claim 1; and
the energy treatment instrument to which the first electric energy and the second electric energy are supplied from the energy control device,
the energy treatment instrument including:
an end effector configured to come in contact with the treated target;
the electrode provided in the end effector, and configured to pass the high-frequency current through the treated target by being supplied with the first electric energy; and
the functioning element configured to generate the treatment energy different from the high-frequency current by being supplied with the second electric energy.

18. The treatment system of claim 17, wherein the functioning element includes a heat generating body configured to generate heat as the treatment energy by being supplied with the second electric energy, and configured to transmit the generated heat to the end effector.

19. The treatment system of claim 17, wherein the functioning element includes an ultrasonic transducer configured to generate ultrasonic vibration as the treatment energy by being with the second electric energy, and configured to vibrate the end effector by transmitting the generated ultrasonic vibration to the end effector.

20. An actuating method of an energy control device, the energy control device being configured to control supply of energy to an energy treatment instrument, the energy treatment instrument including an electrode and a functioning element, the actuating method comprising:
outputting first electric energy, and then passing a high-frequency current through a treated target by supplying the output first electric energy to the electrode;
outputting second electric energy different from the first electric energy, and then generating treatment energy different from the high-frequency current in the functioning element by supplying the output second electric energy to the functioning element; and
controlling an output of the first electric energy and an output of the second electric energy,
the controlling the output of the first electric energy and the output of the second electric energy including:
carrying out a single outputting phase in which only the first electric energy is output;
detecting an impedance of the treated target with time in the single outputting phase;
transitioning the single outputting phase to a simultaneous outputting phase in which the first electric energy and the second electric energy are simultaneously output and the treated target is denatured due to both of the high-frequency current and the treatment energy; and
setting a control pattern relating to the treatment energy in the simultaneous outputting phase, based on at least one of the impedance at a certain time point in the single outputting phase and a variation with time of the impedance in the single outputting phase, and controlling the output of the second electric energy in the simultaneous outputting phase, based on the set control pattern.

* * * * *